(12) United States Patent
Young et al.

(10) Patent No.: US 7,768,942 B2
(45) Date of Patent: Aug. 3, 2010

(54) IDENTIFYING COMPONENTS OF A NETWORK HAVING HIGH IMPORTANCE FOR NETWORK INTEGRITY

(75) Inventors: Malcolm P. Young, Newcastle Upon Tyne (GB); Peter E. Andras, Newcastle Upon Tyne (GB); Mark A. O'Neill, Newcastle Upon Tyne (GB)

(73) Assignee: E-Therapeutics PLC, Newcastle upon Tyne (GB)

( * ) Notice: Subject to any disclaimer, the term of this patent is extended or adjusted under 35 U.S.C. 154(b) by 110 days.

(21) Appl. No.: 12/267,926

(22) Filed: Nov. 10, 2008

(65) Prior Publication Data

US 2009/0062136 A1  Mar. 5, 2009

Related U.S. Application Data

(62) Division of application No. 11/118,071, filed on Apr. 29, 2005, now Pat. No. 7,466,663.

(51) Int. Cl.
*H04J 1/16* (2006.01)
*H04L 12/56* (2006.01)

(52) U.S. Cl. ................ 370/252; 370/254; 370/241
(58) Field of Classification Search ............... 370/252, 370/254, 241
See application file for complete search history.

(56) References Cited

U.S. PATENT DOCUMENTS

| | | | |
|---|---|---|---|
| 5,748,844 A | 5/1998 | Marks | |
| 6,038,390 A | 3/2000 | Sofman | |
| 6,065,063 A | 5/2000 | Abali | |
| 6,167,492 A | 12/2000 | Keller et al. | |
| 6,229,791 B1 | 5/2001 | Nusekabel et al. | |
| 6,437,804 B1 | 8/2002 | Ibe et al. | |
| 7,466,663 B2 | 12/2008 | Young et al. | |
| 2003/0069848 A1* | 4/2003 | Larson et al. | 705/50 |
| 2005/0286414 A1* | 12/2005 | Young et al. | 370/216 |

FOREIGN PATENT DOCUMENTS

| | | |
|---|---|---|
| EP | 0 507 110 A2 | 10/1992 |
| EP | 0 637 153 A1 | 2/1995 |
| EP | 0 652 665 A2 | 5/1995 |
| EP | 0 887 749 A2 | 12/1998 |
| EP | 1 158 447 A1 | 11/2001 |
| WO | WO 0193504 | 12/2001 |
| WO | WO 0197463 | 12/2001 |

OTHER PUBLICATIONS

European Search Report, Jan. 14, 2009.
Zien et al. "Identification of Drug Target Proteins," ERCIM News, Oct. 2000, No. 43, www.ercim.org/publications/ERCIM_NEWS/enw43/zien.html (accessed Jul. 26, 2005).

(Continued)

*Primary Examiner*—John Pezzlo
(74) *Attorney, Agent, or Firm*—Brooks, Cameron & Huebsch, PLLC

(57) ABSTRACT

A computer system (2) is provided which is arranged to receive network data (1) identifying nodes and links between nodes. The computer system (2) processes the input network data (1) to utilise the network topology to identify nodes and links having high importance for network integrity. A report (4) identifying the critical components can then be output.

18 Claims, 19 Drawing Sheets

OTHER PUBLICATIONS

Schroeder, M. A., et al, "Enhanced network survivability through balanced resource criticality", Oct. 15, 1989, pp. 682-687.

Noakes, M. D., et al., "An adaptive link assignment algorithm for dynamically changing topologies", Oct. 23, 1988, pp. 683-689.

Van Helden, J., et al., "Representing and analysing molecular and cellular function using the computer", Biol. Chem., vol. 381 Sep./Oct. 2000, pp. 921-935.

Dogan, A. et al., "Matching and scheduling algorithms for minimizing execution time and failure probability of applications in heterogeneous computing", IEEE Transactions on Parallel and Distributed Systems, vol. 13, No. 3, Mar. 2002, pp. 308-323.

Tarjan, R., "Depth-first search and linear graph algorithms", Switching and Automata Theory, 1971. 12th Annual Symposium on, IEEE, Piscataway, NJ, USA, Oct. 13, 1971, pp. 114-121.

Vilar, J., "Minimal cuts up to third order in a planar graph", IEEE Transactions on Reliability, vol. R-33, No. 3 Aug. 1984, pp. 250-256.

Zien, et al., "Identification of drug target proteins", ERCIM News No. 43, Oct. 2000, pp. 1-3.

European Search Report for related EP Application No. 09172242.1-2416, Jan. 19, 2010, 7 pages.

European Search Report for related EP Application No. 09172247.0-24162157734, Apr. 8, 2010, 9 pages.

* cited by examiner

US 7,768,942 B2

IDENTIFYING COMPONENTS OF A NETWORK HAVING HIGH IMPORTANCE FOR NETWORK INTEGRITY

This application is a Divisional of U.S. Ser. No. 11/118,071, filed Apr. 29, 2005, the specification of which is incorporated by reference herein.

TECHNICAL FIELD

The present invention relates to methods of analyzing networks of interconnected components to identify components of a network which are of high importance for maintaining the network's integrity. The invention also relates to apparatus for carrying out such methods.

INTRODUCTION

Many sorts of systems can be represented in the form of networks comprising nodes interconnected by links. Examples of such networks are social interactions where the nodes might be individuals and the links interactions between those individuals, the Internet where nodes are computers and the links are communication links between computers, and proteome data where nodes indicate proteins and links indicate exchanges of metabolites or interactions between the proteins.

It has been found that in complex systems often a relatively small proportion of the components in a complex system are vital to its function. Thus for example most single protein species in an intra cellular metabolic network can be removed without affecting the function of the system, as can individual exchanges in a telecommunications network. The reason for this is that there are frequently many alternative routes around any removed or dysfunctional element in a complex system, which alternative routes can yield the same metabolic, physical or informational result.

BRIEF DESCRIPTION OF THE DRAWINGS

Aspects and embodiments of the present invention will become apparent with reference to the accompanying drawings in which.

DETAILED DESCRIPTION OF THE DISCLOSURE

Figure 1:
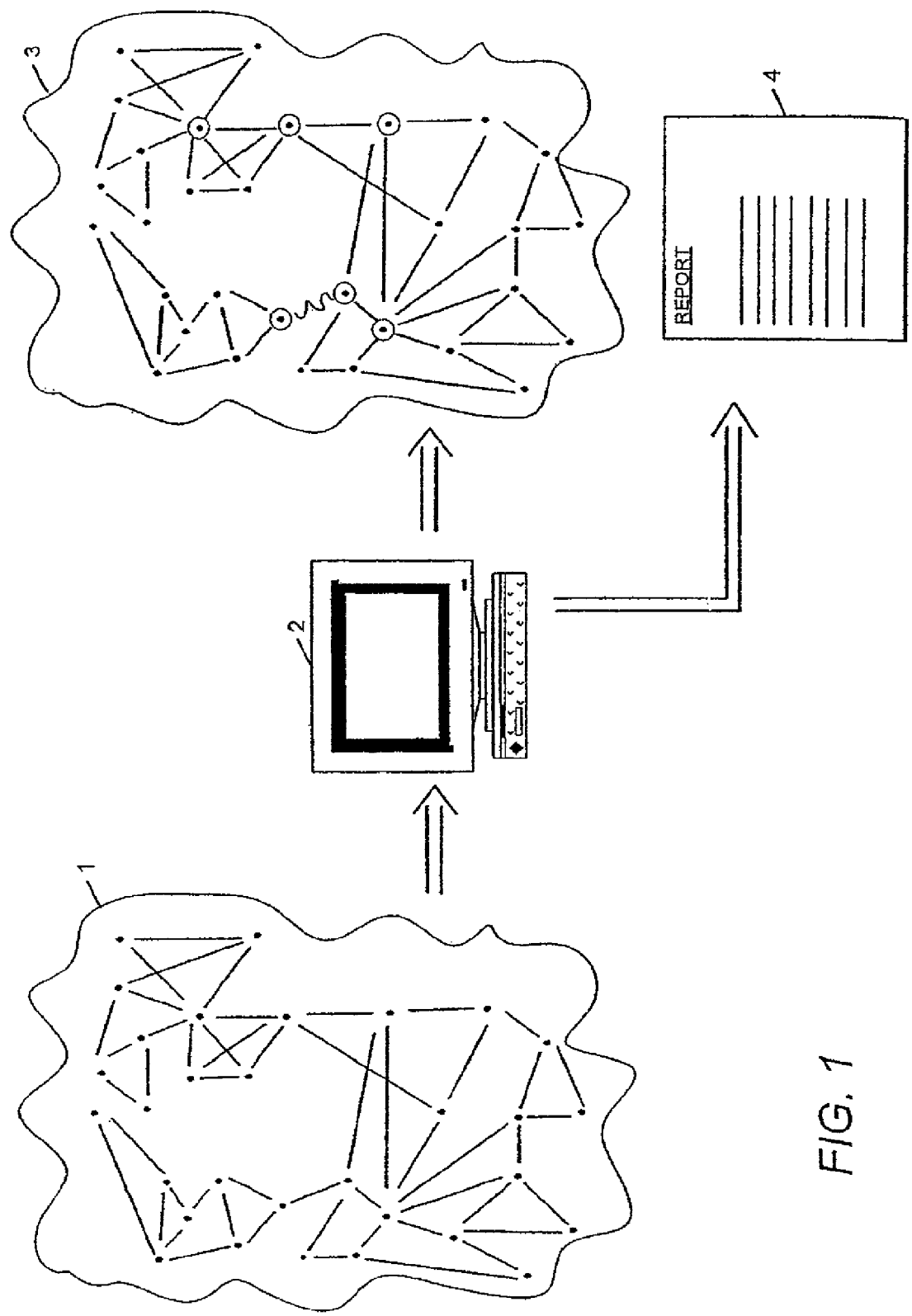
FIG. 1 is a schematic diagram of the processing of data representing nodes interconnected by links by a computer to identify network components of high importance for the integrity of a network.

It is desirable to provide a computer system which can analyse data representative of a network to identify those components which are of high importance for network integrity. In the case of a communications network, if such components can be identified, additional backup can be built to protect the functioning of the vital nodes. In the case of network data representing the proteome of a living organism, the identification of important elements in a network representing the proteome enables potential targets for drug intervention to be identified.

In accordance with one aspect of the present invention there is provided a method of network analysis comprising:
  storing network data defining a plurality of nodes and a plurality of links between the nodes, each node being associated with a network component;
  processing the stored network data to determine for each of the nodes a value indicative of the proportion of paths between other nodes in the network which pass through the node; and
  identifying as network components of importance, network components associated with nodes of the network data for which the number of paths between other nodes which pass through the node relative to the number of paths between the other nodes which do not pass through the nodes is greater than a threshold value.

In accordance with another aspect of the present invention there is provided a method of network analysis comprising:
  storing network data defining a plurality of nodes and a plurality of links between the nodes, each node being associated with a network component;
  processing the stored network data to determine for each of the links a value indicative of the proportion of paths between nodes in the network which pass through the link; and
  identifying as network components of importance network components associated with links of the network data for which the number of paths between nodes which pass through the link relative to the number of paths between the nodes which do not pass through the link is greater than a threshold value.

In accordance with another aspect of the present invention, there is provided a method of network analysis comprising:

storing network data defining a plurality of nodes and a plurality of links between the nodes, each node being associated with a network component;

processing the stored network data to identify sets of nodes connected by links wherein the sets have more connections with nodes within the same set than with nodes in other sets and wherein nodes in different sets are less connected to nodes in other sets than with nodes in the same set; and identifying as network components of importance, network components associated with nodes of the network data providing connections between nodes in different sets of nodes.

In accordance with another aspect of the present invention there is provided a method of network analysis comprising:

storing network data defining a plurality of nodes and a plurality of links between the nodes, each node being associated with a network component;

processing the stored network data to identify a group of nodes of importance for the structural integrity of the network defined by the network data;

identifying for each of the nodes in the network the number of links between each node and the nodes of the identified group of nodes; and identifying as further network components of importance, network components associated with nodes having a number of links to nodes in the identified group of nodes wherein the number of links exceeds a predetermined threshold.

In accordance with a further aspect of the present invention there is provided a method of identifying groups of network components of importance for the structural integrity of a network comprising:

storing network data defining a plurality of nodes and a plurality of links between the nodes, each node being associated with a network component;

determining for each of a number of groups of nodes, a value indicative of the extent to which removal of the group from the network defined by the stored network data affects the structural integrity of the network;

randomly modifying at least some of the groups of nodes to generate further groups of nodes and determining the extent to which the values indicative of structural integrity are affected by the modification; and selecting as groups of nodes of importance for the structural integrity of the network defined by the stored network data groups of nodes associated with values above a threshold value.

In accordance with further aspects of the present invention, there are provided information processing apparatus for storing network data defining a plurality of nodes, and a plurality of links between the nodes and for processing stored network data to identify nodes within a network defined by the stored network data, nodes of importance for the structural integrity of a network in accordance with any of the above described methods.

In accordance with another aspect of the present invention, there is provided a method of identifying target proteins for drug therapies comprising:

obtaining proteome data defining proteins and interactions between proteins for an organism to be targeted;

storing the proteome data defining proteins and interactions between proteins in the form of network data associating each of the proteins with a node and identifying the interactions between the proteins by links between the nodes;

processing the stored network data to identify nodes within the network data of importance for the structural integrity of the network defined by the stored network data; and outputting as data identifying target proteins data identifying the proteins corresponding to the nodes determined to be of importance for the structural integrity of the stored network.

FIG. 1 is a schematic illustration of an embodiment of the present invention. In this embodiment data representing a network 1 in the form of nodes (shown as dots in FIG. 1) interconnected by links (shown as lines in FIG. 1) is input into a computer 2. For illustrative purposes, the data defining a network 1 in this embodiment is taken to be data defining a proteome. That is to say in this embodiment the nodes are indicative of proteins within an organism and the links identify which proteins interact with one another.

Once data representing a network (proteome) has been input into the computer 2, the computer 2 processes the data representing the network to identify within the network a series of nodes and links which are of particular importance for the structural integrity of the network. In FIG. 1, processed data is illustrated by network 3 where the identified nodes of importance for structural integrity of the network are illustrated by circles highlighting some of the nodes. In addition, in FIG. 1 a link in the network is highlighted as a critical link by a wavy line in the output data 3.

As will be described in detail later, the nodes and links identified as being of importance to the structural integrity of the network 1 by the processing of the computer 2 are established in a number of different ways. Once the critical nodes and links have been identified by the processing of the computer 2, the computer 2 can then output a report 4 identifying the critical nodes and links. In the case of a network 1 representing a proteome of an organism, this report will identify potential drug targets for disrupting the functioning of the organism the proteome 1 represents.

The pharmaceutical industry faces the difficult task of identifying cellular targets for drug intervention. Ordinarily, in a particular cell type, there may be proteome data which identifies between 4000 and 6000 potential proteins which could be possible targets. Checking the effect of disrupting the operation of each protein is therefore very time consuming and expensive, particularly as normally organisms are able to compensate for the disruption of individual proteins.

Previously, heuristic approach and serendipity have been the only means of focussing on potential targets for intervention which are likely to yield biological effects when intervened upon by pharmaceutical chemicals. Targeting multiple proteins in a drug treatment can be more successful. However, the number of potential combinations which could be tested is enormous. Given the costs involved, a more focussed approach is desirable.

The applicants have appreciated that certain topological features of a network enable certain nodes and links to be identified as likely suitable targets since these nodes and links can be identified as being of importance to the structural integrity of a network represented by node and link data. Further, the applicants have determined methods by which groups of target nodes of importance for structural integrity can be identified.

Further, by having the computer 2 store data identifying the critical proteins which are utilised and conserved in a host organism, as will be described the potential targets identified by the computer can be filtered so that the report 4 suggests target proteins of the organism represented by the proteome 1 which are not conserved or utilised by a host organism and hence are more likely not to cause side effects in a host. Additionally, the computer 2 can be arranged to include in the report 4 details of agents which are known to attack the functions of the identified critical proteins.

Use of System in Treatment Identification

Figure 2:
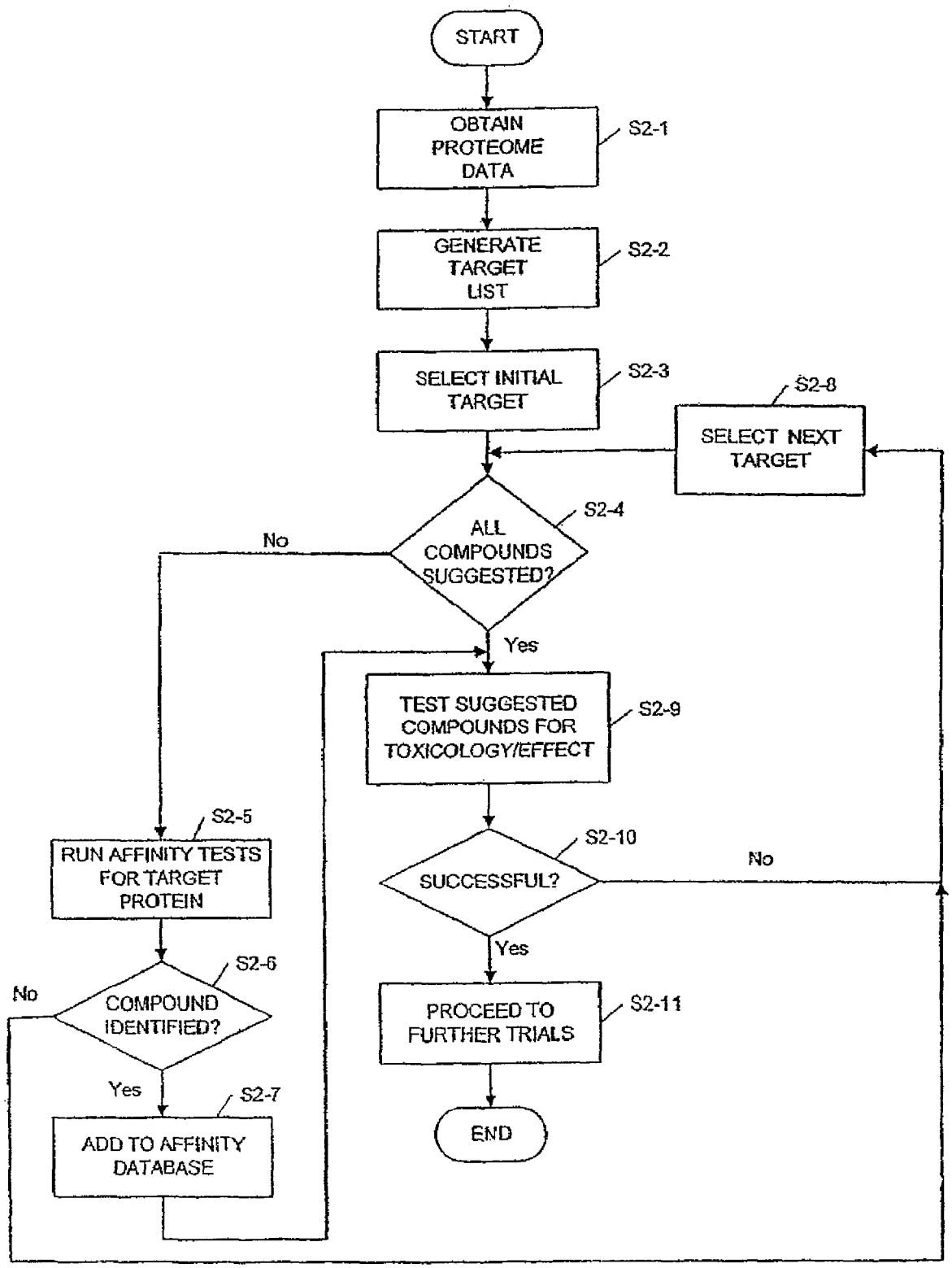
FIG. 2 is a flow diagram of a method of utilising the computer of FIG. 1 as part of a system for identifying pharmaceutical compounds and screening those compounds to identify effective drug treatments.

Before describing the structure and functionality of the above computer system 2 in detail, the use of the above system in identifying potential compounds for treating infections will now be described in with reference to FIG. 2.

Initially (S2-1) proteome data 1 for a target organism is acquired utilising conventional techniques. This proteome data 1 will identify the proteins present within an organism and also the interactions between those proteins. Identification of the proteins can be achieved using conventional techniques such as mass spectrometry and chromatography etc. Whether different proteins interact can then be established using laboratory techniques such as by manipulating proteins so as to be represented in yeast and seeing whether generated proteins interact. When data for the proteome has been acquired it is then entered into the computer 2 and stored.

The computer 2 then (S2-2) processes the input data in the manner described above so as to generate target data which is output in the form of a report 4. This report will identify lists of potential targets which by virtue of the analysis of the network topology of the stored proteome data 1 will highlight potential targets for intervention.

An initial target identified by the report 4 is then selected (S2-3) and checking the report 4 it is determined (S2-4) whether or not any agents are known to react with the identified protein.

If this is not the case affinity tests can then be run (S2-5) against an expression of the identified protein or proteins to attempt to identify (S2-6) possible compounds that interact with the target. If it is determined that a compound suitable for interacting with the identified target can be found, this data is then added (S2-7) to a compound affinity database for future reference. Alternatively if no such compounds can be found, the next target (S2-8) from the report 4 can be selected for analysis.

Either when one or more compounds for attacking specific targets are suggested by the report 4 or alternatively when suitable compounds have been identified through affinity tests the compound or groups of compounds for targeting the identified protein or proteins can then be tested (S2-9) for toxicology and effect to see whether the combination of compounds does indeed disrupt the activity of the organism represented by the proteome data. If the tests (S2-10) are not successful another set of potential targets from the report 4 can be selected (S2-8) and further potential compounds for therapies can be identified.

If the selected compounds have a desired effect on the organism and are not excessively toxic further trials (S2-11) for the identified compounds can be undertaken to establish whether indeed the identified set of compounds is an effective treatment.

Structural Components of Computer System

Figure 3:
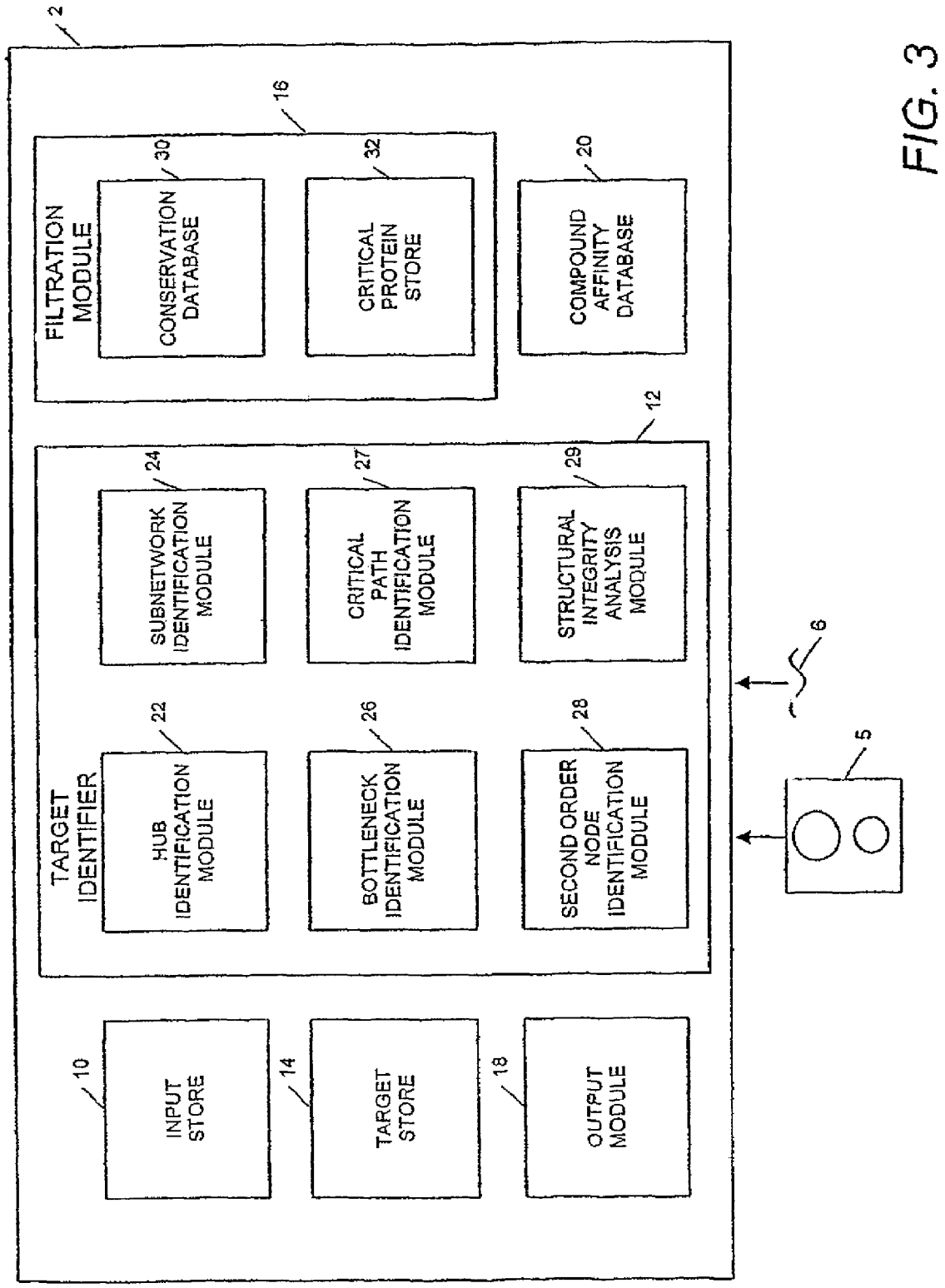
FIG. 3 is a schematic block diagram of the computer modules stored within the memory of the computer of FIG. 1.

The structure of the computer system of FIG. 1 will now be described in detail. Referring to FIG. 3 which is a schematic block diagram of the memory of the computer of FIG. 1, the computer 2 is programmed to operate in accordance with programming instructions input for example as data stored in a data storage medium such as a disc 5 and/or as a signal 6 input into the computer 2 for example from a remote database by transmission over a communications network (not shown) such as the Internet.

As will be described in more detail below, the programming instructions comprise instructions to cause the memory of the computer 2 to become configured to process input data defining nodes and links in a network. The input data is then processed to generate data identifying critical nodes and links within the network. In the case of input network data defining a proteome where the nodes represent proteins and link interactions between proteins, the identified critical nodes and links will then provide information about potential drug targets.

When programmed by the programming instructions, the memory of the computer 2 effectively becomes configured into a number of functional units for performing processing operations. Examples of such functional units are shown in FIG. 3. The units illustrated in FIG. 3, are however, notional and are shown for illustration purposes only to assist understanding; they do not necessarily represent exact units and connections into which the processor, memory etc of the computer 2 become configured.

Referring to the functional units shown in FIG. 3, an input store 10 is provided for storing data defining network data. In this embodiment which is arranged to process proteome data, this network data comprises data identifying proteins in an organism and known interactions between those proteins.

A target identifier 12 is provided which is arranged to process the network data stored within the input store 10 to identify critical proteins and protein interactions having high importance for the integrity of the proteome. Data identifying the critical proteins is then stored within a target store 14. When the target identifier 12 has stored within the target store 14 data identifying critical proteins, the data within the target store 14 is then filtered utilising a filtration module 16 to identify critical proteins and proteins which are conserved within a host organism.

Finally, an output module 18 utilises the filtered data within the target store 14 and a compound affinity database 20 containing data identifying compounds known to react with proteins to generate and output a report 4 which could be displayed on a screen (not shown) or printed on a printer (not shown) listing the identified critical proteins together with suggested compounds for therapies based on drug targets identified by the target identifier 12.

In this embodiment, the target identifier 12 comprises six sub modules 22-29 each arranged to identify a different type of structure within network data which is indicative of particular components in the network being of high importance for the structural integrity of the network.

The sub modules comprise a hub identification module 22 which is arranged to identify proteins which interact with large numbers of other proteins; a sub network identification module 24 for identifying connections between sub networks; a bottleneck identification module 26 and a critical path identification. module 27 for identifying nodes and links within the network data in the input store 10 which cannot be easily bypassed and hence are of importance for the integrity of the network; a second order node identification module 28 for identifying nodes representing proteins directly interacting with nodes identified by the hub identification module 22, sub network identification module 24 and bottleneck identification module 26; and a structural integrity analysis module 29 for identifying groups of nodes which together significantly affect the structural integrity of the network represented by the data within the input store 10.

As will be described after targets and proteins have been identified by the target identifier 12 and stored within the target store 14, the targets are filtered by a filtration module 16. In this embodiment, the filtration module 16 comprises a conservation database 30 and a critical protein store 32.

The conservation database 30 is arranged to store data identifying similar proteins which are conserved between different organisms. Thus for example data is stored identifying that a particular protein in an organism is substantially a homolog of another protein in a host such as a human. The critical protein store 32 is a database storing data identifying critical proteins for the activity of a host. When data identifying a number of target proteins has been generated and stored within the target store 14, the stored targets are likely to be proteins and metabolites which will disrupt the activity of the organism identified by the proteome data and the input store 10 by virtue of the manner of the processing by the target identifier 12. However, although such targets may be useful for enabling general disinfectants to be identified, if a suitable drug is to be developed it must not only be effective against a target organism, but also must not have excessive side effects.

In order to aid with the identification of more promising drug targets, the filtration module 16 stores in the conservation database 30 data for identifying which proteins have similar proteins in the host organism, Where a potential target protein is identified which is not present in any form in a host organism it is more likely that a therapy disrupting that particular protein will have limited side effects. If it is not possible to identify a protein which is not conserved as a potential target, at the very least it is desirable to ensure that the targets chosen for further research are unlikely to disrupt the critical systems of a host. By storing data in a critical protein store 32 identifying the critical proteins for a host the list of potential targets can be appropriately filtered to highlight the most promising potential therapies.

Processing to Identify Critical Nodes and Links

Figure 4:
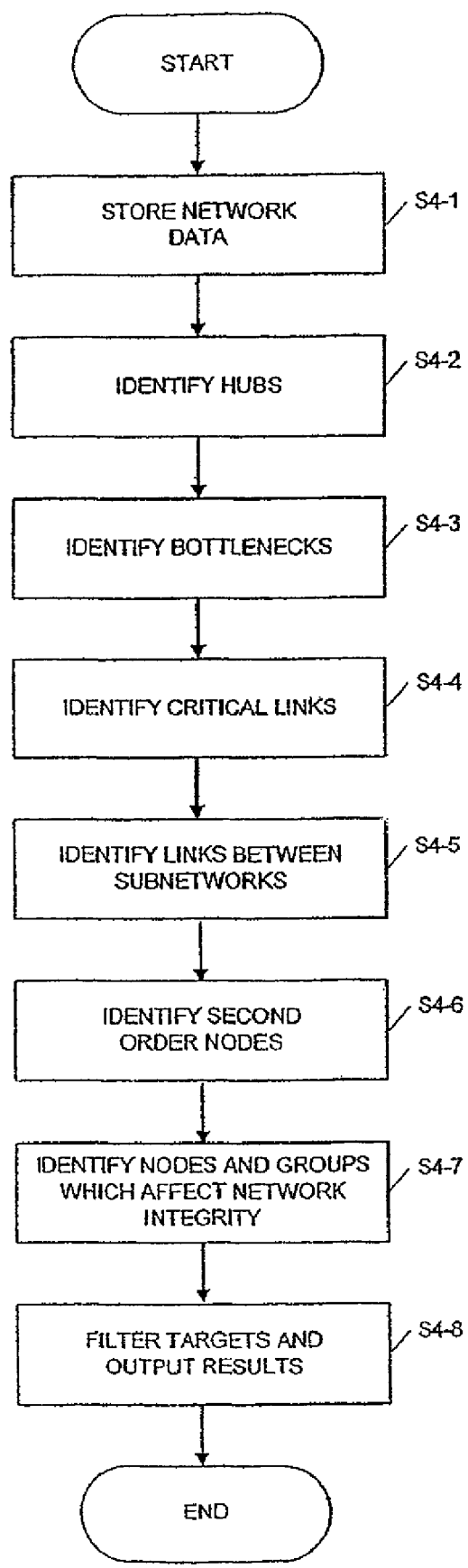
FIG. 4 is a flow diagram of the processing of the computer of FIG. 1.

The processing of the computer 2 will now be described in greater detail with reference to FIG. 4 which is a flow diagram illustrating the processing of the computer 2.

Initially (S4-1) data representing the network to be analysed is stored within the input store 10.

Figure 5:
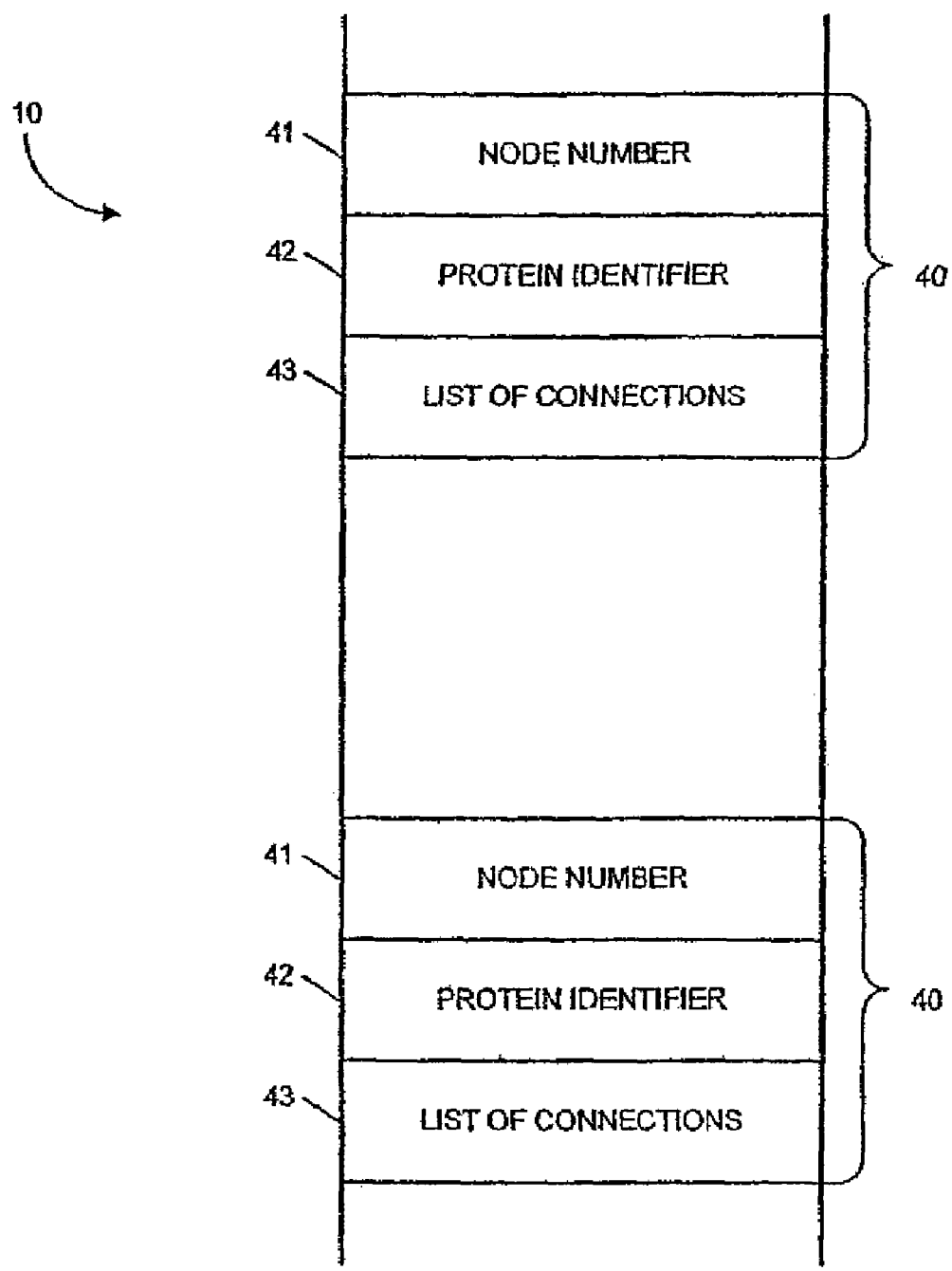
FIG. 5 is a schematic block diagram of network data stored within the memory of the computer of FIG. 1.

FIG. 5 is a schematic illustration of data stored within the input store 10. In this embodiment the data stored within the input store 10 is stored in the form of a number of node records 40 each comprising a node number 41, a protein identifier 42 and a list of connections 43. One of these records 40 is stored for each of the proteins within the proteome being analysed. In each record 40 the list of connections 43 is a list of node numbers 41 of the node records 40 of the proteins with which the protein identified by the protein identifier 42 for the record 40 is known to interact with. Such data can be obtained for a proteome for a particular organism or cell utilising conventional laboratory techniques, In other embodiments where the network data stored within the input store 10 is representative of a network other than a proteome, the protein identifier 42 will be replaced with a different identifier of a network component and the list of connections 42 would be a list of node numbers 41 of components within the network an identified component interacts with.

(a) Hub Identification

Once data for the proteome has been stored within the input store 10, the target identifier 12 then invokes the hub identification module 22 to identify (S4-2) hub nodes within the network.

Figure 6:
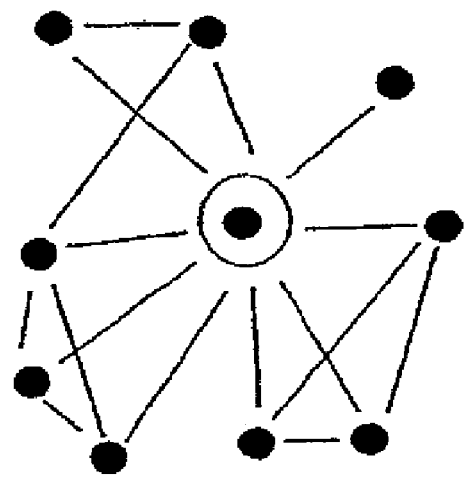
FIG. 6 is a schematic illustration of a portion of a network identifying a Ahub@ node.

FIG. 6 is a schematic illustration of a portion of a network. In FIG. 6 nodes are represented by circles and links between nodes are indicated by lines connecting the circles. As shown in FIG. 6 some nodes such as the node highlighted by a larger circle interact with significantly more nodes than average. Where nodes represent proteins such well connected nodes are often indicative of proteins critical to the functioning of an organism. By identifying such nodes, potential drug targets can therefore be found.

Thus, in this embodiment, when the hub identification module 22 is invoked, the hub identification module 22 initially determines for each of the node records 40 within the input store 10 the number of entries in the list of connections 43 for each record 40. A list of node numbers is then ordered according to the number of entries in the list of connections 43 in the records 40 identified by the node numbers 41.

Thus in this way the node numbers 41 of nodes which have the greatest numbers of connections and hence are indicative of hubs within the network can be identified. Data identifying the node numbers of nodes with the greatest number of connections is then stored in the target store 14.

In this embodiment which is arranged to process proteome data where normally approximately around about 4000-6000 proteins are included in a proteome and hence 4000-6000 node records 40 will ordinarily be stored in the input store 10. When this number of nodes is stored the hub identification module 22 in this embodiment is arranged to store within the target store 14 the node numbers identifying the twenty nodes having the greatest number of entries in their list of connections 43.

(b) Bottleneck Identification

Returning to FIG. 4, after storing data indicative of the hub nodes in the target store 14, the target identifier 12 then (S4-3) invokes the bottleneck identification module 26 to identify within the network represented by data stored within the input store 10 further portions of a network which are important for the structural integrity of that network.

Figure 7:
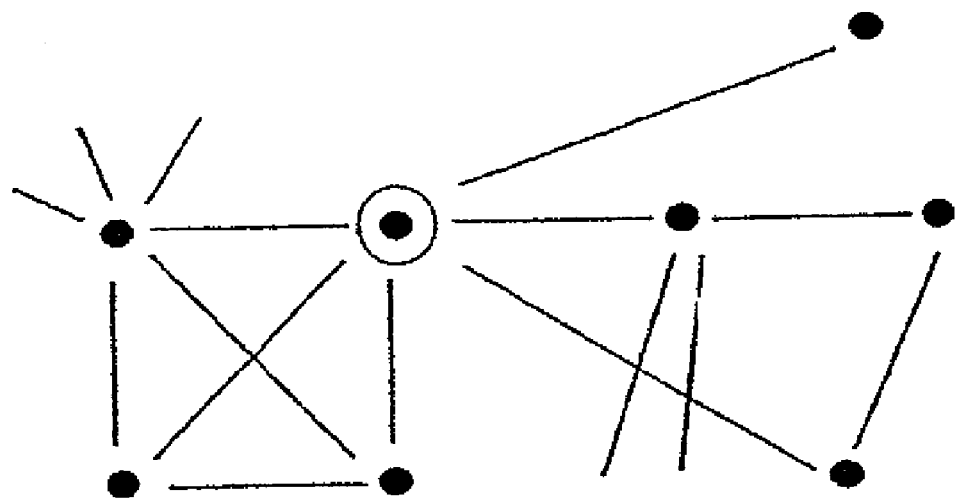
FIG. 7 is a schematic illustration of a portion of a network identifying a low redundancy node in a network.

Specifically, the bottleneck identification module 26 is arranged to identify nodes in the network which cannot be easily bypassed. An example of such a node within a network is illustrated in the exemplary network of FIG. 7 where all the paths from the nodes shown as dots in the network of FIG. 7 pass through a single node highlighted by a circle, If communication through the node highlighted by the circle is disrupted this then has a significant impact on the integrity of the rest of the network as many nodes will no longer be able to communicate with one another.

The processing of the bottleneck identification module 26 will now be described in greater detail with reference to FIGS. 8 and 9 which are a flow diagram of the processing of data by the bottleneck identification module 26 and a schematic illustration of a portion of an exemplary network respectively.

Figure 8:
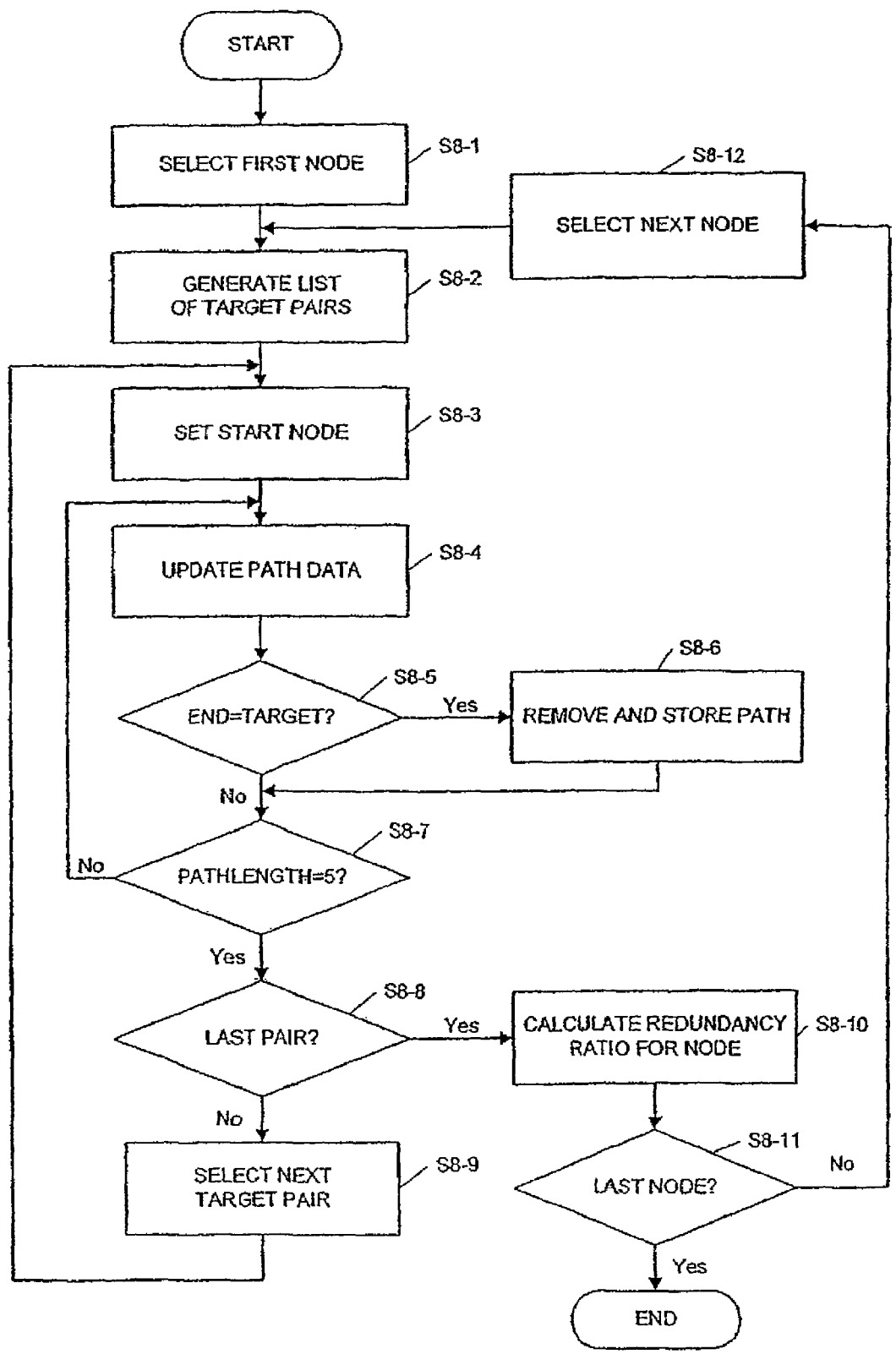
FIG. 8 is a flow diagram of the processing of the computer of FIG. 1 to identify low redundancy nodes.

Referring to FIG. 8, when the bottleneck identification module 26 is initially invoked (S8-1) the bottleneck identification module 26 selects a first node for processing, In this embodiment this is achieved by the bottleneck identification module 26 selecting the node record 40 having a node number 41 equal to one.

Figure 9:
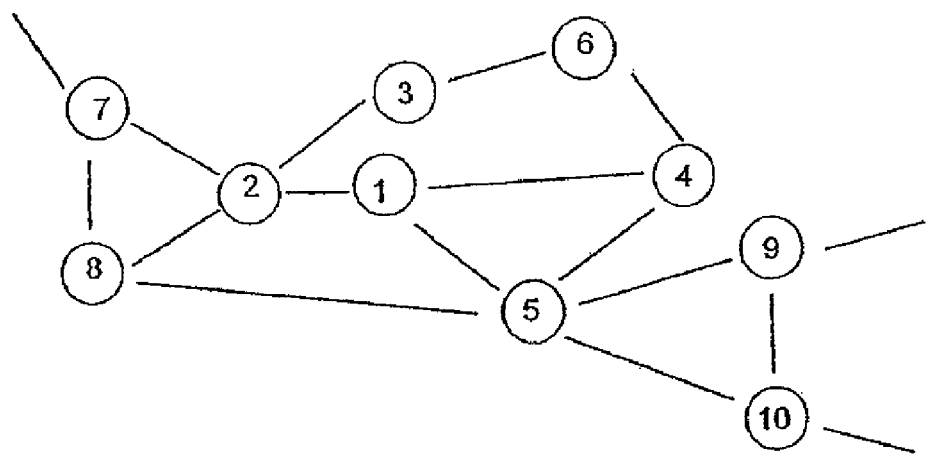
FIG. 9 is a schematic illustration of an exemplary portion of a network for illustrating the processing of FIG. 8.

Thus for example, in the illustrative network of FIG. 9 where nodes are indicated by numbers surrounded by circles and links between nodes are shown as lines between the circles, the bottleneck identification module 26 would select for processing the node identified by the number 1 in FIG. 9.

The bottleneck identification module 25 then (S8-2) generates a list of target pairs. Specifically, the bottleneck identification module 26 processes the list of connections 43 of the node record 40 currently being processed and generates a set of target pairs comprising pairs of distinct node numbers identified from the list of connections 43.

Thus for example, in the case of the exemplary network of FIG. 9 where node 1 is shown as being connected to nodes 2, 4 and 5, the node record 40 having a node number 41 set equal to 1 would have a list of connections 43 of the following form [2,4,5]. The bottleneck identification module 26 would therefore generate as a list of target pairs the following set of target pairs [(2,4), (2,5), (4,5)].

Once a list of target pairs has been generated, the bottleneck identification module 26 then (S8-3) selects the first target pair and sets as a start node the first value in the target pair. The bottleneck identification module 26 then generates an initial item of path data comprising a list consisting of this selected start node.

Thus in the case of processing the target pair (2,4) the bottleneck identification module 26 would select as a start node the node number 2 and generate a single item of path data comprising list: [2].

The bottleneck identification module 26 then proceeds to process all the currently existing items of path data by taking each of the items of path data in turn. For each item of path data, the final entry in the list of nodes comprising the path data is then identified. The item of path data is then replaced by a number of items of path data consisting of the current item of path data to which is appended data representative of the different nodes from the list of connections 43 for the node record 40 of the last entry in the item of path data being processed.

Thus, in the case of processing the item of path data consisting of a single entry [2] and the exemplary network of FIG. 9, the list of connections 43 for the node record 40 having a node number set equal to 2, would be [1,3,7,8] When processing the item of path data [2], this item of path data would therefore be replaced by the following items of path data:

[2,1]
[2,3]
[2,7]
[2,8]

The bottleneck identification module 26 then checks each of the newly generated items of path data and deletes any items of path data which contain any node number more than once. In the case of the above exemplary list of generated items of path data, since none of these contain a node number more than once no items of path data would be deleted.

When all of the existing path data has been updated, the bottleneck identification module 26 then (S8-5) determines whether the final entry in any of the newly generated items of path data corresponds to the second value of the target pair currently being processed.

Thus in the case of processing the target pair (2,4) the bottleneck identification module 26 would check whether any of the entries in each of the generated items of path data was equal to 4.

If this is found to be the case, the bottleneck identification module 26 then removes the identified item of path data from further processing and stores it separately for later consideration (S8-6).

After any items of path data having a final value equal to the second entry in the target pair being processed has been identified and stored, the bottleneck identification module 26 checks (S8-7) whether path data having five entries has been generated. If this is not the case, the bottleneck identification module 26 then processes the currently existing items of path data in the same way as has previously been described (S8-4-S8-6), generating new items of path data by appending further node numbers to the existing items of path data before checking once again whether the current length of items of generated path data is now equal to five entries (S8-7).

Thus in the case of processing the items of path data described above at the second iteration when processing the target pair (2,4), the following items of path data would be generated:

[2,1,4], [2,1,5], [2,3,6], [2,7,8], [2,8,5], [2,8,7] of which the path data [2,1,4] would be identified as ending with the value 4 and stored separately for later processing.

Eventually, the bottleneck identification module 26 will determine that path data having five entries has been generated. At this stage, the bottleneck identification module 26 will have stored path data identifying every path between nodes identified by the current target pair having no more than five elements.

In the case of processing the target pair (2,4) of the exemplary network of FIG. 9, the following data would therefore have been stored:

[2,1,4], [2,8,5,4], [2,7,8,5,4], [2,3,6,4], [2,8,5,1,4].

The bottleneck identification module 26 then (S8-8) checks whether the target pair being processed is the final target pair generated for the current node. If this is not the case, the next target pair is then selected (S8-9) and processed in the same way as the previous target pair (S8-3-S8-8). As a result further path data, identifying paths between the two nodes identified by the next target pair will be generated and stored.

Thus in the case of the example network of FIG. 9, processing the target pair (2,5) would cause the following items of path data to be stored.

[2,1,5], [2,3,6,4,5], [2,7,8,5], [2,8,5], [2,1,4,5].

When the bottleneck identification module 26 determines (S8-8) that all generated target pairs for a particular node have been processed, the bottleneck identification module 26 then (S8-10) proceeds to use the stored items of path data to calculate a redundancy ratio for the node being processed.

Specifically, the bottleneck identification module 26 determines the number of stored items of path data which include the current node being processed relative to the total number of stored items of path data.

Thus in the case of processing node 1 of FIG. 9 where the following path data would be stored:

[2,1,4], [2,8,5,4], [2,7,8,5,4], [2,3,6,4], [2,8,5,1,4], [2,1,5], [2,3,6,4,5], [2,7,8,5], [2,1,8,5], [4,1,5], [4,5], [4,1,2,8,5]

a redundancy ratio of 5/12=0.42 would be determined.

This value is indicative of the proportion of paths between nodes connected to the node for which the ratio is calculated which pass through that node. Thus in the case of a high ratio value, this will indicate that there are very few paths which can bypass that node and hence that the node is of relatively high importance for the structural integrity of that portion of the network. The value therefore provides an indication of whether disruption of the node is likely to disrupt communication through the network.

After the bottleneck identification module 26 has calculated a redundancy ratio for a node, the bottleneck identification module 26 checks (S8-11) whether a redundancy ratio has been calculated for all the nodes in the network. If this is not the case, the next node record 40 for the next node number 41 is selected for processing (S8-12) and a redundancy ratio for that node is determined (S8-2-S8-10) before the bottleneck identification module 26 checks once again (S8-11) that redundancy ratios for all nodes have been calculated.

When a redundancy ratio for each of the nodes has been determined, the bottleneck identification module 26 can then use the stored redundancy ratio data to identify the nodes in the network which cannot easily be bypassed. In this embodiment data identifying the node numbers of the nodes associated with the redundancy ratios indicating the twenty nodes which are hardest to bypass is then stored in the target store 14.

(c) Critical Link Identification

Returning to FIG. 4, after the bottleneck identification module 26 has identified and stored data identifying any nodes which are difficult to bypass in the network, the critical path identification module 27 is then invoked and attempts to identify (S4-4) individual links within the network which are difficult to bypass.

Figure 10:
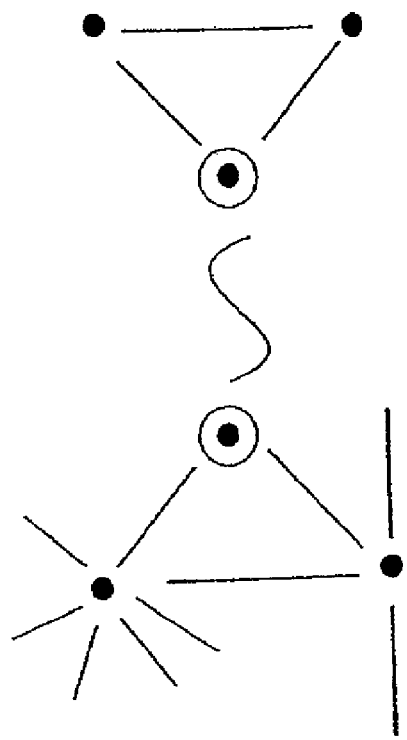
FIG. 10 is a schematic illustration of a portion of network identifying a low redundancy link in a network.

FIG. 10 is a schematic illustration of a portion of a network where a critical link between two nodes is highlighted. In the case of FIG. 10 the highlighted nodes are surrounded by larger circles and the highlighted link is illustrated by a wavy line.

When processing data to identify nodes that are difficult to bypass such as that illustrated in FIG. 10, often these critical nodes will be connected to one another. In such circumstance in addition to identifying the nodes as of importance for the structural integrity of the network, the individual link between two nodes can also be identified as a potential weakness within the network.

Figure 11:
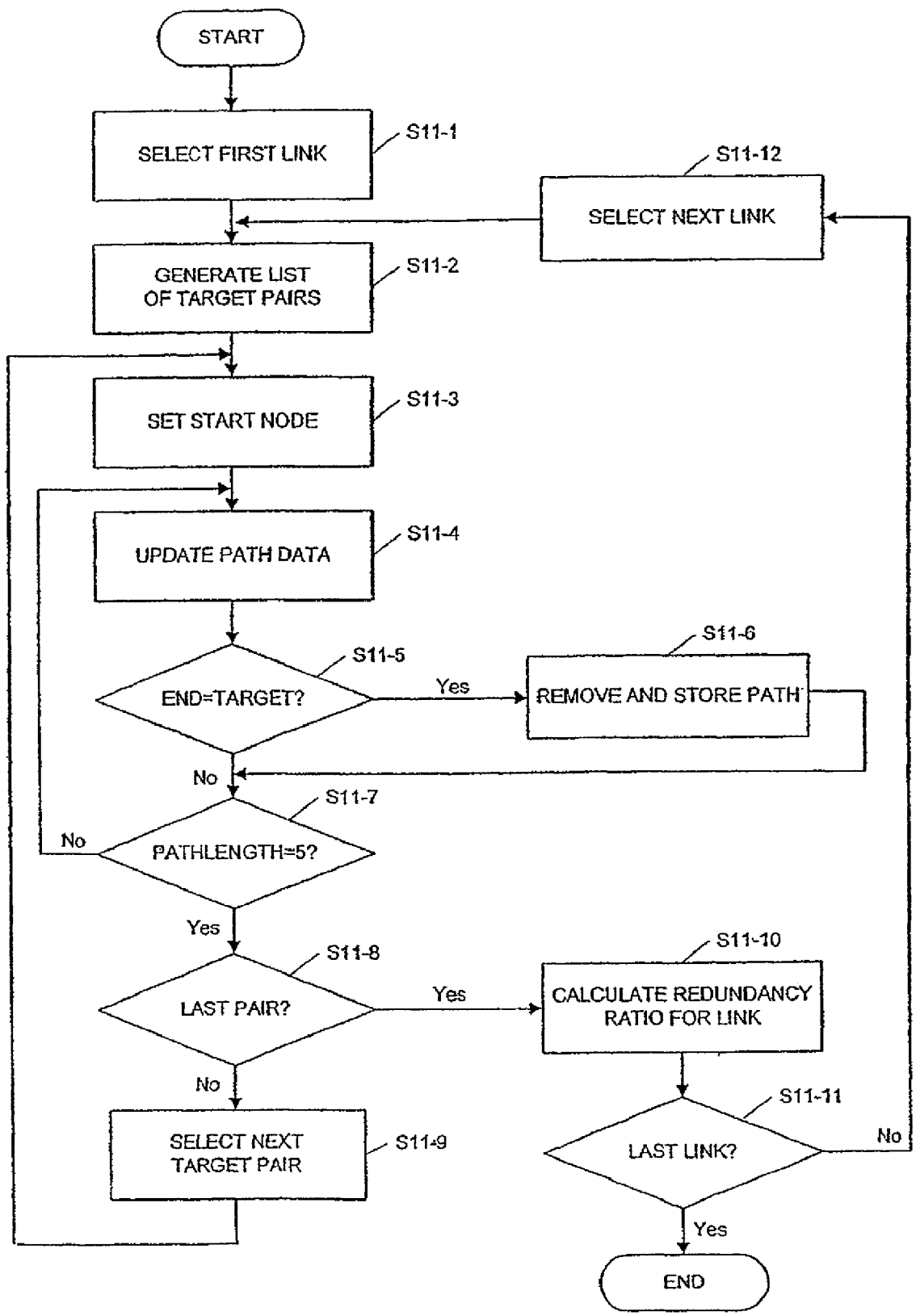
FIG. 11 is a flow diagram of the processing of the computer of FIG. 1 to identify low redundancy links.

The processing of the critical path identification module 27 will now be described in detail with reference to FIG. 11 which is a flow diagram of the processing of the critical path identification module 27.

The processing of the critical path identification module 27 is very similar to the processing undertaken by the bottleneck identification module 26. However, instead of processing each of the nodes in turn, the critical path identification module 27 processes each link within the network.

When the critical path identification module is first invoked a first link (S11-1) is selected. In this embodiment this link is the link identified by the node number 41 of the first node record 40 and the first entry in the list of connections 43 associated with that node record 40 where the identified entry in the list of connections 43 is a node number no greater than the node number 41 for the node record 40 currently being processed.

Thus for example processing the network of FIG. 9, the node record 40 for node 1 would be selected and then the link [1-2] would be identified for processing.

The critical path identification module 27 then generates a list of target pairs (S11-2) in a similar way to the generation of target pairs previously described in relation to the processing of the bottleneck identification module 26. However, in this case instead of generating a list of target pairs utilising the nodes identified in the list of connections 43 of the node record 40 currently being processed, the critical path identification module 27 generates a set of target pairs utilising the lists of connections 43 of both of the nodes identified by the link currently being processed. This list of target of pairs is generated by determining all possible distinct pairs of nodes that can be formed by selecting entries from the lists of connections 43 of the two node records 40 identified by the link.

Thus in the case of the exemplary network of FIG. 9 processing the link [1-2], the critical path identification module 27 would utilise the list of connections 43 for the first and second nodes namely the lists: [2,4,5] and [1,3,7,8] to generate the following list of target pairs where each of the entries in each pair are distinct:

(2,1) (4,1) (5,1)
(2,3) (4,3) (5,3)
(2,7) (4,7) (5,7)
(2,8) (4,8) (5,8)

After this list of target pairs has been generated for the link being processed, these target pairs are utilised in exactly the same way as has previously been described in relation to the processing of the bottleneck identification module 26. That is to say the target pairs are used to generate and store a series of items of path data including up to five entries where the head and tail of each list corresponds to a head and tail of one of the target pairs (S11-3-S11-9). In this way the critical path identification module 27 identifies every path of up to four links between each of the nodes connected to the nodes of the link currently being processed.

When path data has been generated and stored for all of the target pairs generated for a particular link, the critical path identification module 27 then (S11-10) calculates a redundancy ratio for the link. This is achieved in a similar way to the calculation of a redundancy ratio by the bottleneck identification module 26. However in the case of the critical path identification module 27, the critical path identification module 27, calculates the proportion of stored items of path data which include a step corresponding to the link currently being processed.

Thus for example when generating a redundancy ratio value for the link (1,2) the critical path identification module 27 determines the proportion of stored of items of path data for a link including within the path data either the entry 2 followed by the entry 1 or the entry 1 followed by the entry 2.

Once a redundancy ratio for a particular link has been calculated, the critical path identification module 27 then checks (S11-11) whether all of the links in the network have been processed. If this is not the case, the critical path identification module 27 then (S11-12) selects the next link for processing and calculates (S11-2-S11-11) a redundancy ratio for that link.

When all of the links have been processed, a redundancy value will be stored for each of the links where a high redundancy ratio values indicates a link within the network which cannot easily be bypassed. Data identifying the 20 links associated with the highest redundancy ratio values is then stored within the target store 14 together with data identifying the nodes identified by those links.

(d) Identification of Links Between Sub Networks

Returning to FIG. 4, after the critical path identification module 27 has identified links within the network which cannot easily be bypassed, the sub network identification module 24 is then invoked which then proceeds to identify (S4-5) nodes and links involved in connecting sub networks as will now be described in detail with reference to FIGS. 12-15.

Figure 12:
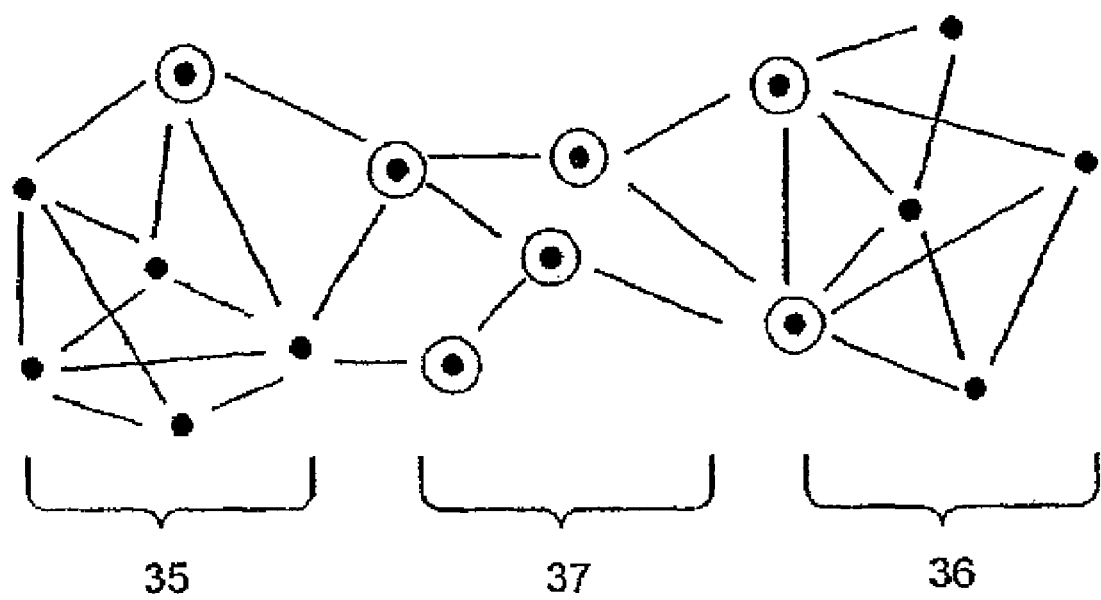
FIG. 12 is a schematic illustration of a portion of a network connecting two sub networks.

FIG. 12 is a schematic illustration of a network divided into two sub networks. In this application the term sub network is taken to mean portions of a network comprising nodes that are more connected to one another than other nodes in the rest of the network. Thus in the case of FIG. 12 the left and right hand sections of the illustrated network 35,36 are examples of sub networks whereas the nodes in the centre of the illustrations 37 are an illustrative example of a bridge between two sub networks. That is to say the nodes shown as highlighted provide a connection between the two sub networks 35,36.

When network data is representative of for example a proteome, the existence of sub networks normally identify a series of proteins and protein interactions responsible for different functions within the organism. Thus for example one sub network might involve proteins responsible for controlling cell division, whereas another sub network might identify proteins responsible for controlling energy generation.

The applicants have appreciated that by identifying nodes responsible for linking the activities of two sub networks, it is possible to identify targets which disturb communications between the sub networks. In the case of an organism, this could for example cause the functions responsible for cell division to no longer be coordinated with the energy generation network and hence cause the organism to no longer reproduce properly.

In this embodiment the sub network identification module 24 is arranged to identify nodes within a network responsible for connecting different sub networks in two distinct ways. The first of these methods will now be described with reference to FIG. 13.

In accordance with this first method for identifying links between sub networks, the sub network identification module 24 initially (S13-1) generates twenty sets of cluster data where each of the nodes is randomly assigned to one of twenty different clusters.

The table below is an illustrative example of twenty sets of cluster data where each of the nodes 1-n has been randomly assigned a cluster value from 1 to 20.

|        | Set 1 | Set 2 | ... | Set 20 |
|--------|-------|-------|-----|--------|
| Node 1 | 10    | 9     | ... | 20     |
| Node 2 | 15    | 5     | ... | 1      |
| Node 3 | 12    | 7     | ... | 1      |
| Node 4 | 10    | 9     | ... | 3      |
| ...    | ...   | ...   | ... | ...    |
| ...    | ...   | ...   | ... | ...    |
| Node k | 9     | 10    | ... | 4      |
| ...    | ...   | ...   | ... | ...    |
| ...    | ...   | ...   | ... | ...    |
| Node n | 1     | 2     | ... | 5      |

The sub network identification module 24 then selects the first set of cluster data (S13-2) and randomly modifies (S13-3) one of the cluster values for one of the nodes in the selected set. The effect of randomly amending the value of the cluster associated with a particular node by the set of data can either be to swap the node between the cluster identified by the data previously into the cluster identified by the new value, or alternatively to assign the node to a new separate cluster.

Thus for example processing set 1 of the table above if node one is randomly selected for modification changing the cluster value associated with node 1 to 15 will have the effect of placing node 1 in the same cluster as node 2. Conversely by randomly changing the cluster value for the node 1, to say for example 21, node 1 would be placed in a new cluster separate from any of the existing clusters.

After a random modification of the cluster data for the current set has been determined, the sub network identification module 24 calculates a cost value for the modification compared with a cost value for the unmodified set. In this embodiment the cost value is determined using the following equation:

where $A_n$=number of nodes connected to node n in different clusters to node n $B_n$=number of nodes unconnected to node n in the same cluster as node n and $\lambda 1$ and $\lambda 2$ are scaling factors whose relative values are set based on the average connectivity of the stored network.

Thus in this way, where a node is assigned to a cluster which predominately contains nodes which are connected to that node and the cluster does not predominately contain nodes to which the node is not connected, the calculated cost value will decrease. Conversely, if a node is assigned to a cluster which predominately contains nodes that it is not connected to rather than nodes that it is connected to, the cost value will increase.

After cost values for the proposed modification have been determined, the sub network identification module 24 then (S13-4) determines whether the proposed modification increases the cost associated with the unmodified cluster data being processed by more than 10% of the cost value associated with the unmodified cluster data. If this is not the case, the sub network identification module proceeds to add (S13-5) the modified cluster set data to the cluster set data previously stored.

After either the cost associated with a modified data set has been determined to be more than 10% greater than the cost associated with the unmodified cluster data being processed, or alternatively after data representing the modified data set has been stored by the sub network identification module 24, the sub network identification module 24 then (S-13-6) determines whether the last of the stored sets of cluster data has been reached (S13-6).

If this is not the case, the next set of cluster data (S13-7) is selected and then modified (S13-3) and a cost is determined for the modified data set (S13-4) and if this cost is exceptable the modified cluster set data is stored (S13-5) before the sub network identification module 24 determines once again (S13-6) whether the last cluster set has been reached.

As a result of this processing and random modification of the cluster set data, the sub network identification module 24 will eventually process all the stored cluster set data and will cause to be stored cluster set data for any random modifications which do not result in an increase in cost score 10% greater than the score associated with a cluster set before the cluster set has been randomly modified.

When this has been achieved, the sub network identification module 24 proceeds to filter (S13-8) the stored sets of cluster data. In this embodiment the filtration of cluster set data is such to eliminate any duplicate sets of data and either all sets of cluster set data associated with a cost value 35% greater than the lowest cost value associated with any of the stored cluster sets, or alternatively to retain only the sets of cluster data associated with the top 100 scores, whichever retains the greatest number of sets of cluster data.

After the stored cluster data has been filtered, the sub network identification module 24 then (S13-9) determines the number of iterations which have been performed to attempt to identify potential sub networks. If this number is not equal to the maximum number of iterations the sub network identification module 24 then proceeds to process all of the stored cluster set data (S13-2-12-8) again before checking once again whether the maximum number of iterations has been reached. In this embodiment, the maximum number of iterations is set to 50.

By randomly modifying the cluster data in this way at each iteration the sub network identification module 24 causes the sets of cluster data associated with the lowest cost values to be retained. By virtue of the manner in which the cost values are calculated this will mean that the retained sets of cluster data will be those where the same cluster numbers are associated with nodes which predominately are connected and which are not connected to nodes assigned different cluster numbers.

Ultimately, as result of the processing by the sub network identification module 24 after the required number of iterations cluster data which most accurately assigns connected nodes to the same clusters and disconnected nodes to different clusters will be stored.

In this embodiment, the sub network identification module 24 then (S13-10) proceeds to utilise the twenty sets of cluster data associated with the highest score values to identify nodes forming links between sub networks.

Specifically, using each of the sets of cluster data in turn, for each of the nodes the number of connections a node has assigned to different clusters can then be calculated. In the case of nodes involved in connections between different sub networks, this number will be higher than in the case of nodes which do not form part of such connections. Data identifying the number of cross sub network connections for each node is then stored. By identifying the nodes associated with the greatest number of connections to other sub networks, those nodes involved in connecting between sub networks can then be identified.

Thus for example if the following cluster data were stored:

|  | Cluster No. |
| --- | --- |
| Node 1 | 1 |
| Node 2 | 1 |
| Node 3 | 2 |
| Node 4 | 3 | and node one was connected to nodes 2, 3 and 4 an interconnection value of 2 would be stored.

The sum of these values determined for nodes utilising each of the top twenty sets of cluster data then provide a good indication of the extent to which each node forms part of a connection between sub networks as in general, the nodes for which high values are determined will be the nodes included in such interconnections.

In this embodiment, after the number of connections each node has with nodes not in the same cluster has been determined for each of the top twenty sets of cluster data, those nodes associated with the top twenty highest sum of numbers are stored within the target store 14 as data indicative of nodes involved in bridges between sub networks.

Figure 13:
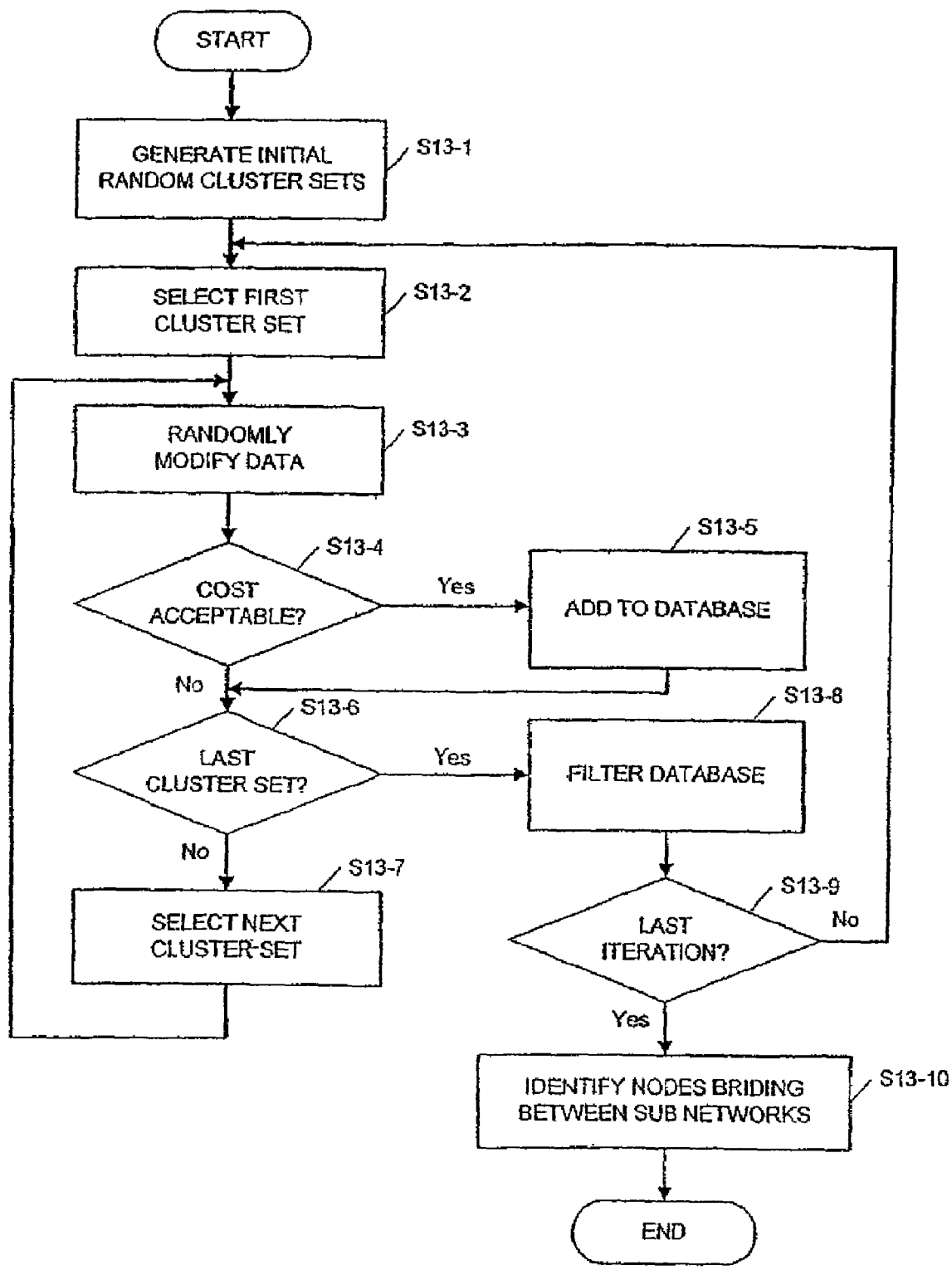
FIGS. 13 and 14 are flow diagrams of the processing of the computer of FIG. 1 to identify sub networks within a network of nodes and links.

After the sub network identification module 24 has identified nodes connecting sub networks utilising the method illustrated in FIG. 13, the sub network identification module 24 then proceeds to identify an alternative set of nodes involved in connections between sub networks will now be described with reference to FIGS. 14 and 15 which are a flow diagram of the processing of the sub network identification module 24 and an illustrative example of a processed network respectively.

Figure 14:
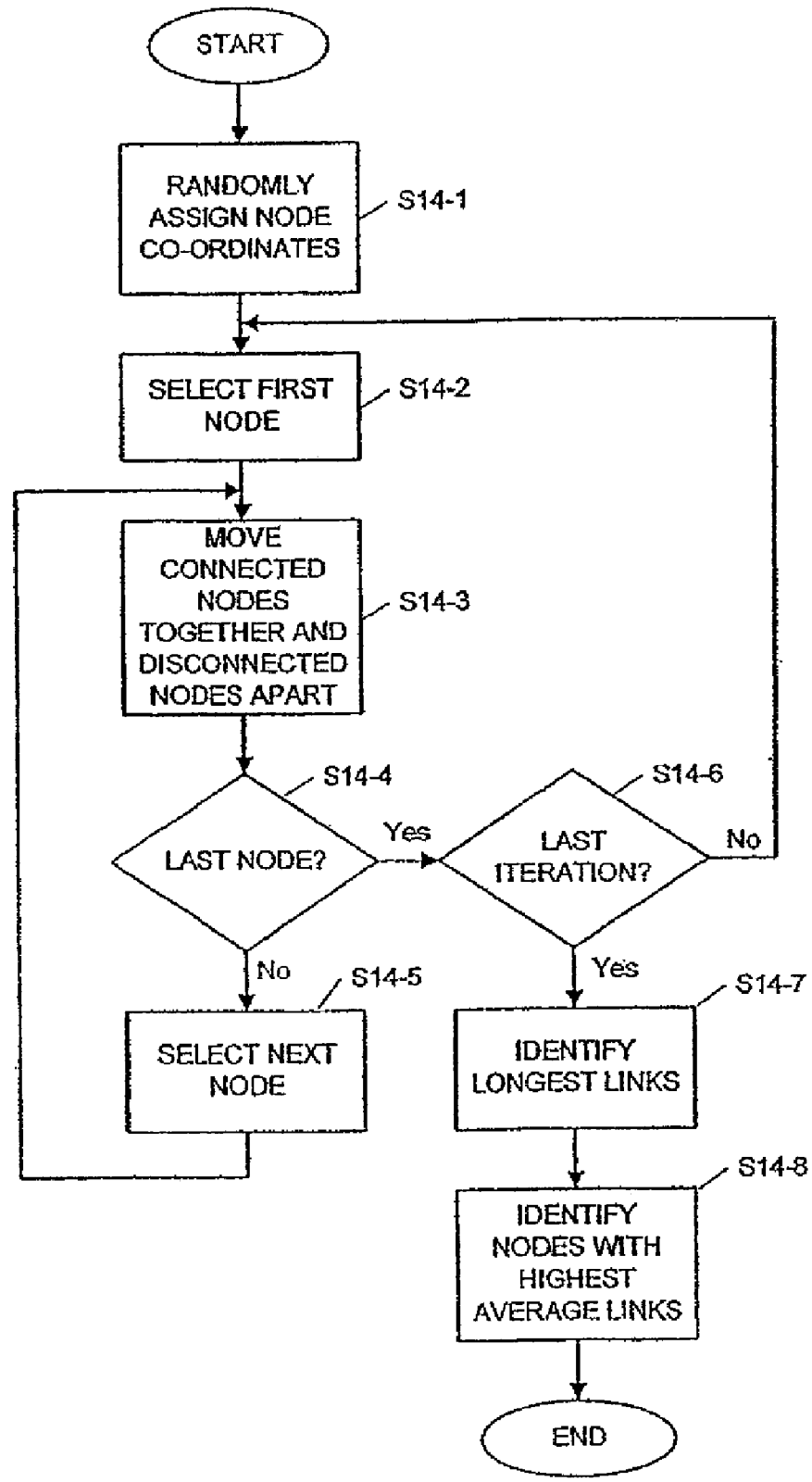

Referring to FIG. 14 in this embodiment in accordance with this method the sub network identification module 24 initially randomly associates each node for which node data is stored within the input store 14 with a random co-ordinate data (S14-1) In this embodiment for ease of illustration, this co-ordinate data is taken to comprise a pair of two dimensional co-ordinates. In other embodiments sets of 3 or more co-ordinates could be utilised.

When all the nodes have been randomly assigned a two dimensional coordinate, the first node is selected (S14-2). The sub network identification module 24 then modifies (S14-3) the coordinate data associated with each of the other nodes for which node data has been stored in the input store utilising the following equation:

$$(x_n, y_n) \Box (x_n+a, y_n+b)$$

where $a=2(x_n-x_p)$ and $b=2(y_n-y_p)$ if node n is connected to the node currently being processed; and $a=2(x_p-x_n)$ and $b=2(y_p-y_n)$ if node n is not connected to the node currently being processed; and $(x_n,y_n)$ and $(x_p, y_p)$ are the co-ordinates associated with node n and the node currently selected for processing respectively.

The effect of updating the co-ordinate data associated with other nodes in this way is to cause the co-ordinate data of connected nodes to be brought closer together and the co-ordinate of unconnected nodes to be moved further apart.

When all of the co-ordinate data for all of the other nodes has been updated the sub network identification module 24 then (S14-4) checks whether the current node being processed is the last node. If this is not the case the next node is selected (S14-5) as the node to be processed and all the co-ordinate data associated with the other nodes is then updated using the newly selected node (S14-3) before the sub network identification module 24 checks once again (S14-4) whether the final node has been reached.

Eventually all of the nodes for which data has stored within the input store 10 will have been processed and the co-ordinate data updated accordingly, The sub network identification module 24 then checks (S14-6) whether there have been fifty iterations of co-ordinate data updating. If this is not the case the first node is selected once again (S13-2) and the co-ordinates of all the nodes are further updated utilising the updated co-ordinate data.

After fifty iterations of updates have been made, the processing of data will be such as to associate linked nodes with similar co-ordinates and unlinked nodes with different co-ordinates.

Figure 15:
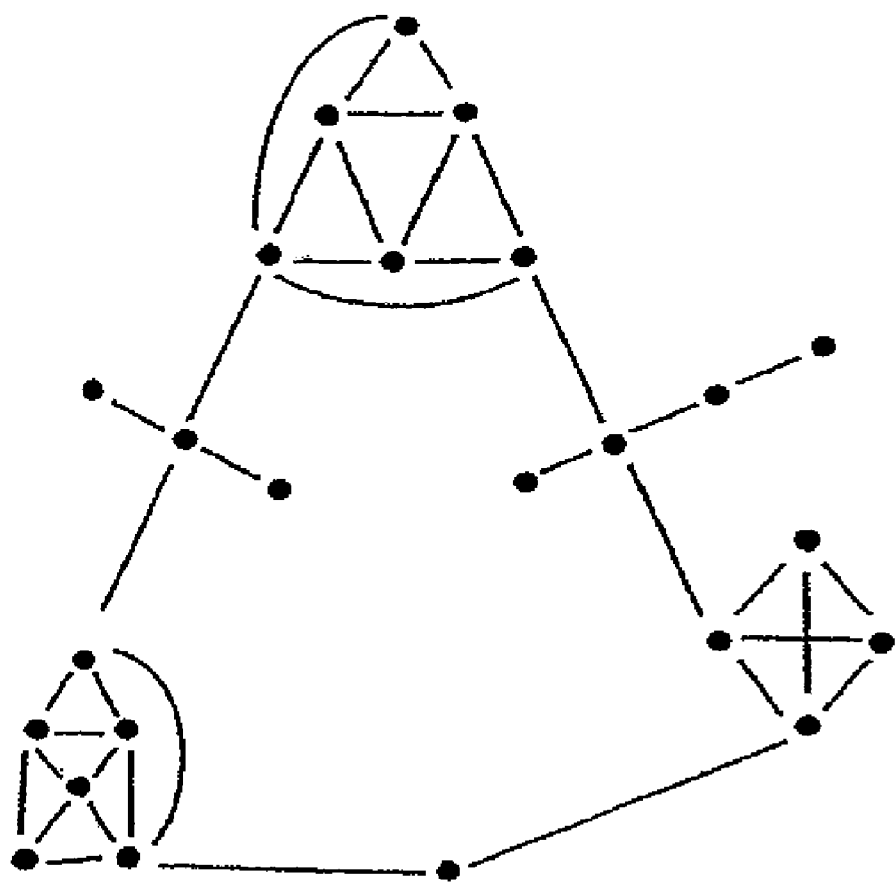
FIG. 15 is a schematic illustration of a network organised into a number of sub networks.

FIG. 15 is a schematic illustration of an exemplary network after processing where the positions of the nodes correspond to two dimensional co-ordinates calculated in accordance with the algorithm shown in FIG. 14. As can visually been seen in the exemplary illustration of FIG. 15, the network of FIG. 15 is shown as comprising three distinct sub networks which are more interconnected with one another than any other part of a network. These three sub networks are themselves interconnected via three distinct pathways.

Returning to FIG. 14, once the final iteration of co-ordinate updates has been made the sub network identification module 24 then (S14-7) proceeds to process each link as identified by network data stored within the input store 10 in turn and determines using the co-ordinate data associated with the nodes corresponding to the link a distance value for each link. Data identifying the twenty links associated with the greatest distance values and also the nodes identified by those links are then stored in the target store 14.

As can be seen from FIG. 15, by identifying the longest links and the nodes associated with them, those nodes and links involved in communicating between sub networks can be identified.

In addition to identifying the longest links and the nodes associated with the longest links, the sub network identification module 24 also (S14-8) determines for each of the nodes the average length of each link associated with that node and also stores within the target store 14 data identifying the nodes associated with the longest average link length.

Again since the nodes associated with many long links are likely to be involved with links between sub networks, processing the network data stored in the input store 10 in this way provides means for identifying nodes involved in connecting sub networks and hence nodes of importance for a network's structural integrity.

(e) Identification of Second Order Nodes

At this stage stored within the target store 14 is data identifying hub nodes, nodes that are difficult to route around and nodes involved in links between sub networks. Each of the sets of nodes will have been identified utilising the node and link data defining a network topology stored in the input store 10.

In addition to these nodes, the applicants have appreciated that a further set of nodes that are important for network integrity are those nodes that are connected to these identified hubs, nodes that are difficult to avoid and links between sub networks. This is because these nodes interact with nodes of importance and hence if the functioning of these connected nodes is disrupted, the functioning of the other identified nodes of importance may also be effected.

In the case of proteome data identifying proteins and protein interactions, frequently, certain proteins corresponding to hubs or other critical nodes are in practice unsuitable for targets as disrupting the activity of such protein can cause unwanted side effects in a host. The secondary proteins which interact with these critical proteins may, however, differ between a target organism and a host. By interfering with the manner in which these proteins interact with the identified critical nodes, the activities of these critical nodes can be effected in a way does not cause a corresponding disruption of the activity of a host.

Figure 16:
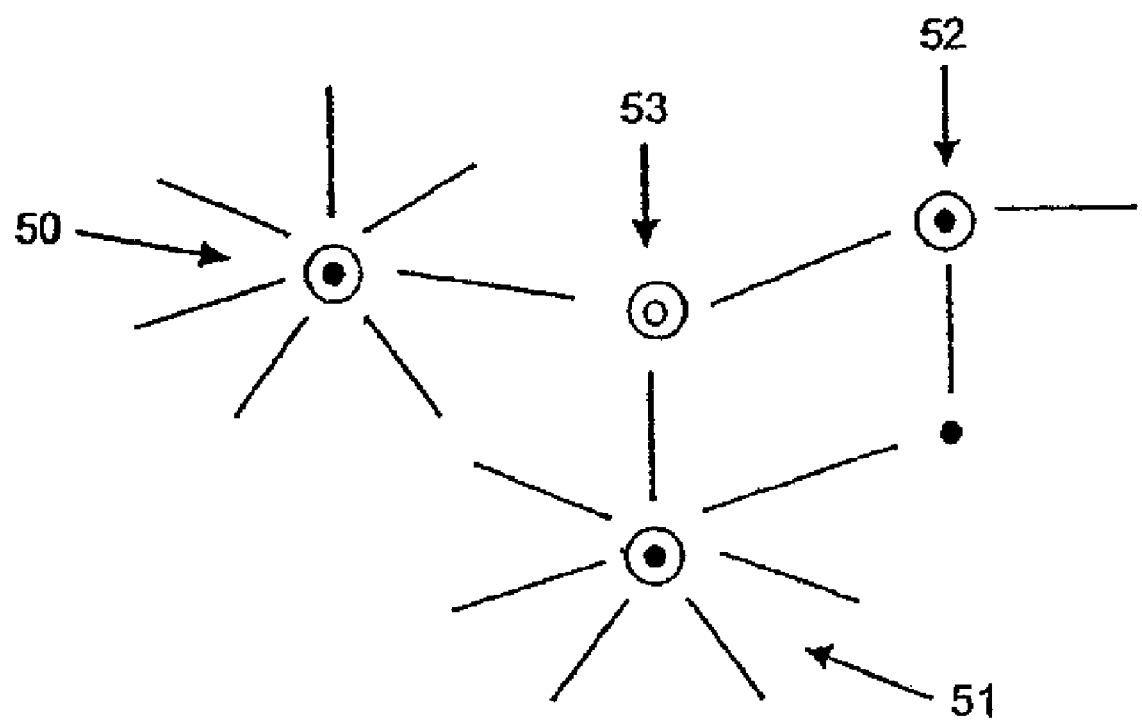
FIG. 16 is a schematic illustration of a portion of a network identifying a second order node.

Thus for example in FIG. 16 there are four nodes, two of these nodes labelled 50 and 51 are examples of hub nodes having many connections. Node 52 is shown as an example of a node which is difficult to route around, In the exemplary network of FIG. 16, node 53 is shown as being connected to nodes 50, 51 and 52, all of which can be identified as being of potential importance by virtue of analysis of the network topology. Given the large number of links node 53 has to nodes identifiable as important, enables node 53 to be identified as a potential target for affecting the structural integrity of the network.

Thus returning to FIG. 4, in this embodiment once the hub nodes, nodes linking sub networks and nodes which are difficult to route around have been identified, the target identifier 12 invokes the second order node identification module 28. The second order node identification module 28 then (S4-6) determines for each of the nodes in the network the number of nodes for which identifying data has been stored in the target store 14 which are contained in the list of connections 43 in each of the node records 40. This data is stored for each of the nodes and the second order node identification module 28 then identifies the top twenty nodes connected to the greatest number of other nodes of importance.

Thus in this way the second order node identification module 28 is able to identify those nodes which are directly linked to a number of other nodes of importance.

(f) Identification of Groups of Nodes for Affecting Network Integrity

At this stage, the target store 14 will have stored within it data identifying the node numbers of all of the nodes identified by the hub identification module 22, sub network identification module 24, bottleneck identification 26, critical path identification module 27 and second order node identification module 28. Although this data identifies individual nodes of importance for maintaining the structural integrity of the network identified by data stored within the input store 10, it is desirable for the target identifier 14 to additionally generate data identifying groups of nodes which together effect the structural integrity of the network. In this embodiment this is achieved by the structural integrity analysis module 29 which proceeds to identify (S4-7) nodes and groups of nodes which effect network integrity as will now be described with reference to FIGS. 17-20.

Figure 17:
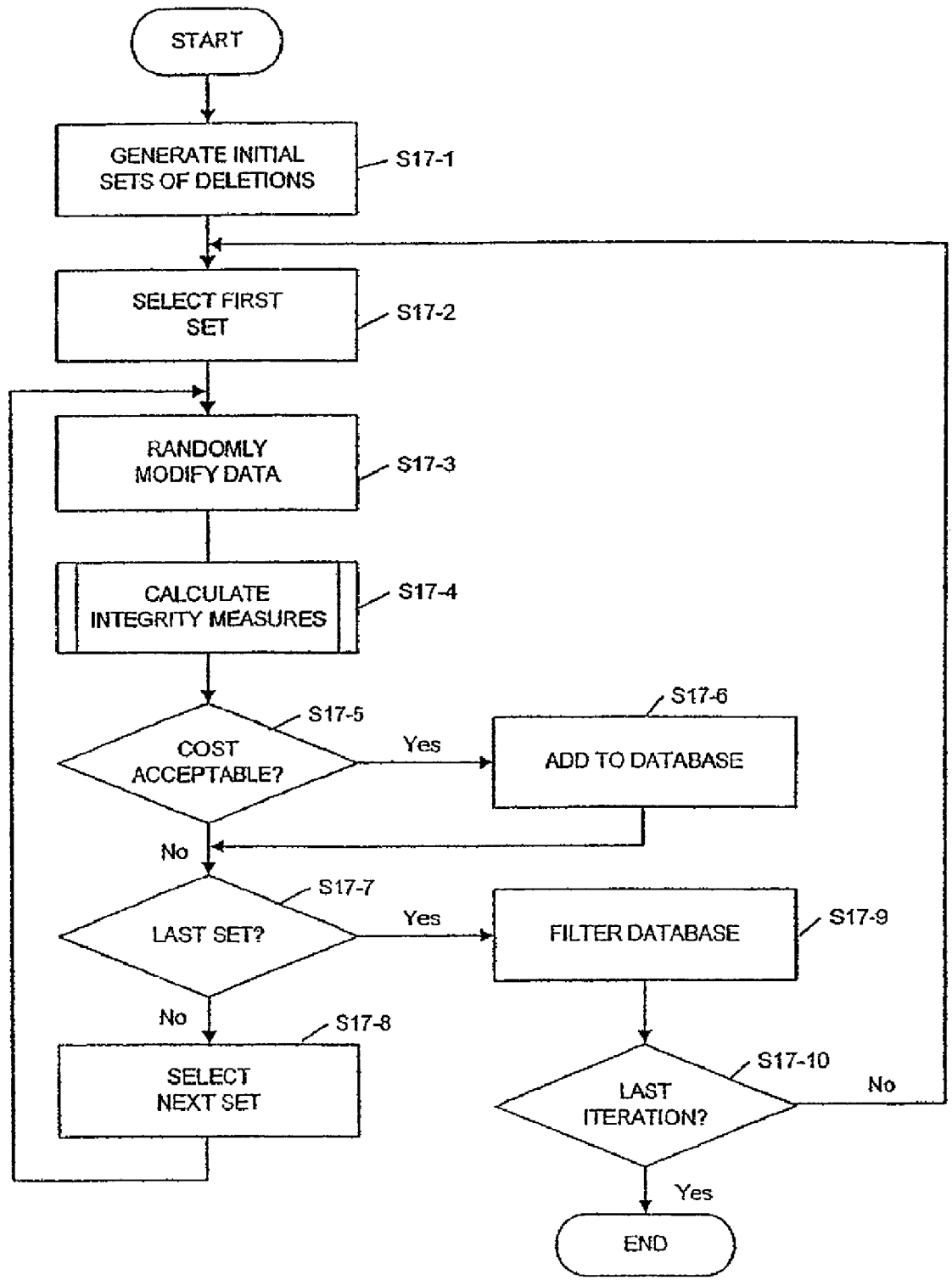
FIG. 17 is a flow diagram illustrating the processing of the computer of FIG. 1 to identify groups of nodes of high importance for network integrity.

Referring to FIG. 17, which is a flow diagram of the processing of the structural integrity analysis module 29, when the structural integrity analysis module 29 is first invoked (S17-1) the structural integrity analysis module 29 initially generates a number of sets of proposed deletions.

In this embodiment the processing illustrated in FIG. 17 is undertaken by the structural integrity analysis module 29 for groups of deletion including from one to ten members where the processing of FIG. 17 is undertaken for each of the different sizes of groups. Thus for example if the structural integrity analysis module 29 were to be processing groups consisting of three nodes, when generating an initial set of deletions, the structural integrity analysis module 29 would determine a number of sets of three nodes to use as a starting point for identifying groups of three nodes which together effect the structural integrity of the network represented by network data stored in the input module 10. In this embodiment the structural integrity analysis module 29 is arranged to generate fifty initial random sets of deletions each containing the required number of members which are then subjected to further processing as will now be described.

After the initial sets of proposed deletions have been generated, the structural integrity analysis module 29 then (S17-2) selects the first set of proposed deletions. This first set is then randomly modified (S17-3).

Thus for example if the first set of proposed deletions comprises deleting nodes 1, 2 and 3, one of the members of the proposed set of deletions is substituted for another node in the network. Thus for example the proposed set of deletions might become 1, 2 and 56.

The structural integrity analysis module 29 then (S17-4) calculates three measures of the effect of the proposed modified set of deletions as will now be described in detail with reference to FIGS. 18, 19 and 20.

Figure 18:
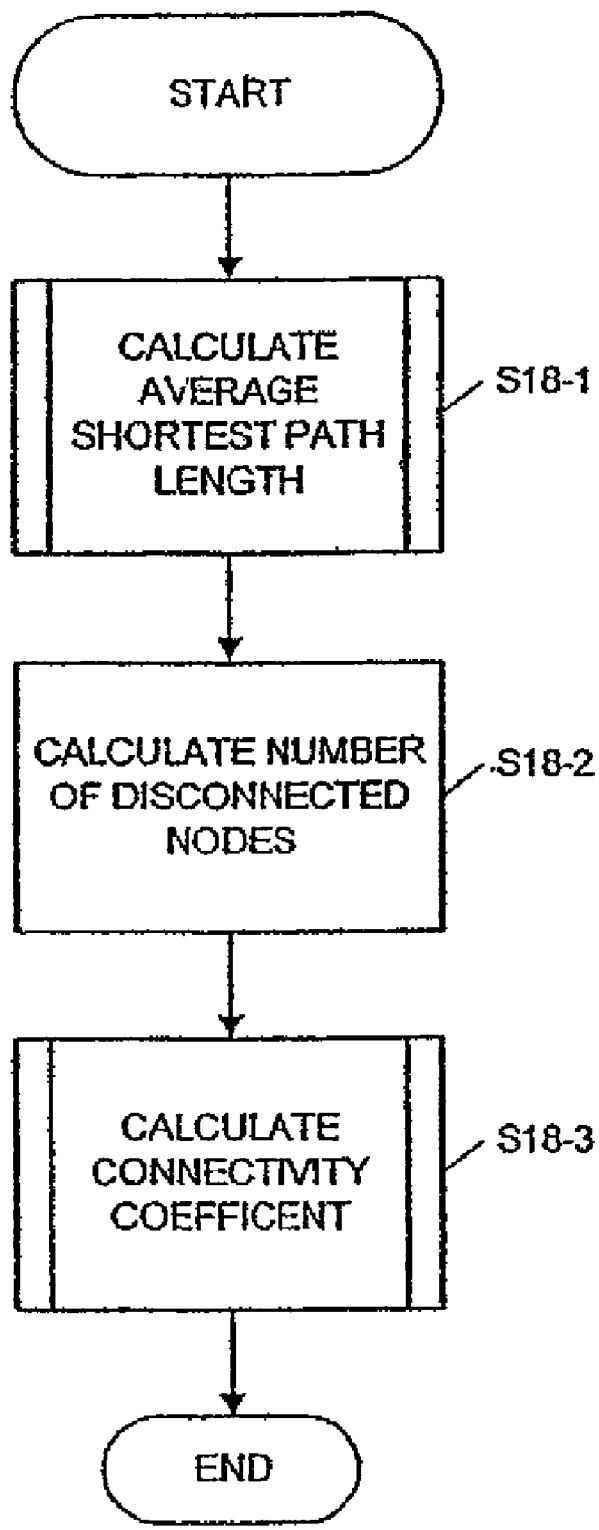
FIG. 18 is a flow diagram of the processing of the computer of FIG. 1 to generate a number of measures of the effect of removing nodes from a network on the integrity of the network.

Initially, referring to FIG. 18 (S18-1) the structural integrity analysis module 29 determines the average shortest path length between the node in the network from which the nodes identified by the proposed deletion are removed. Where proposed deletions affect the structural integrity of the network this average shortest path link measure will increase and hence by measuring the effect of change on the average shortest path length whether the proposed modified set of deletions is or is not an improvement on the proposed set of deletions from which it is derived can be established.

Figure 19:
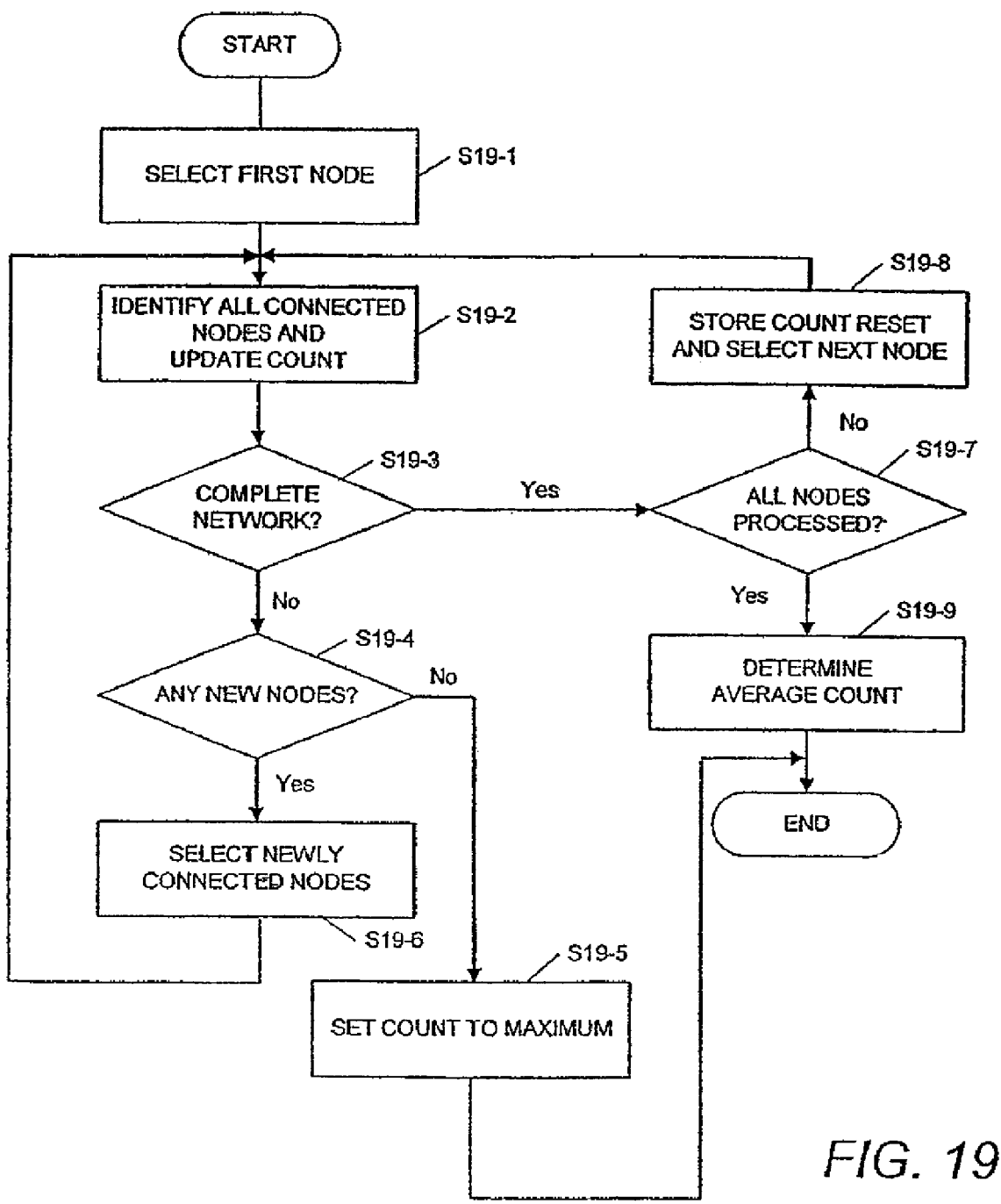
FIG. 19 is a flow diagram of the processing of the computer of FIG. 1 to determine the average shortest path length between nodes in a network.
Figure 20:
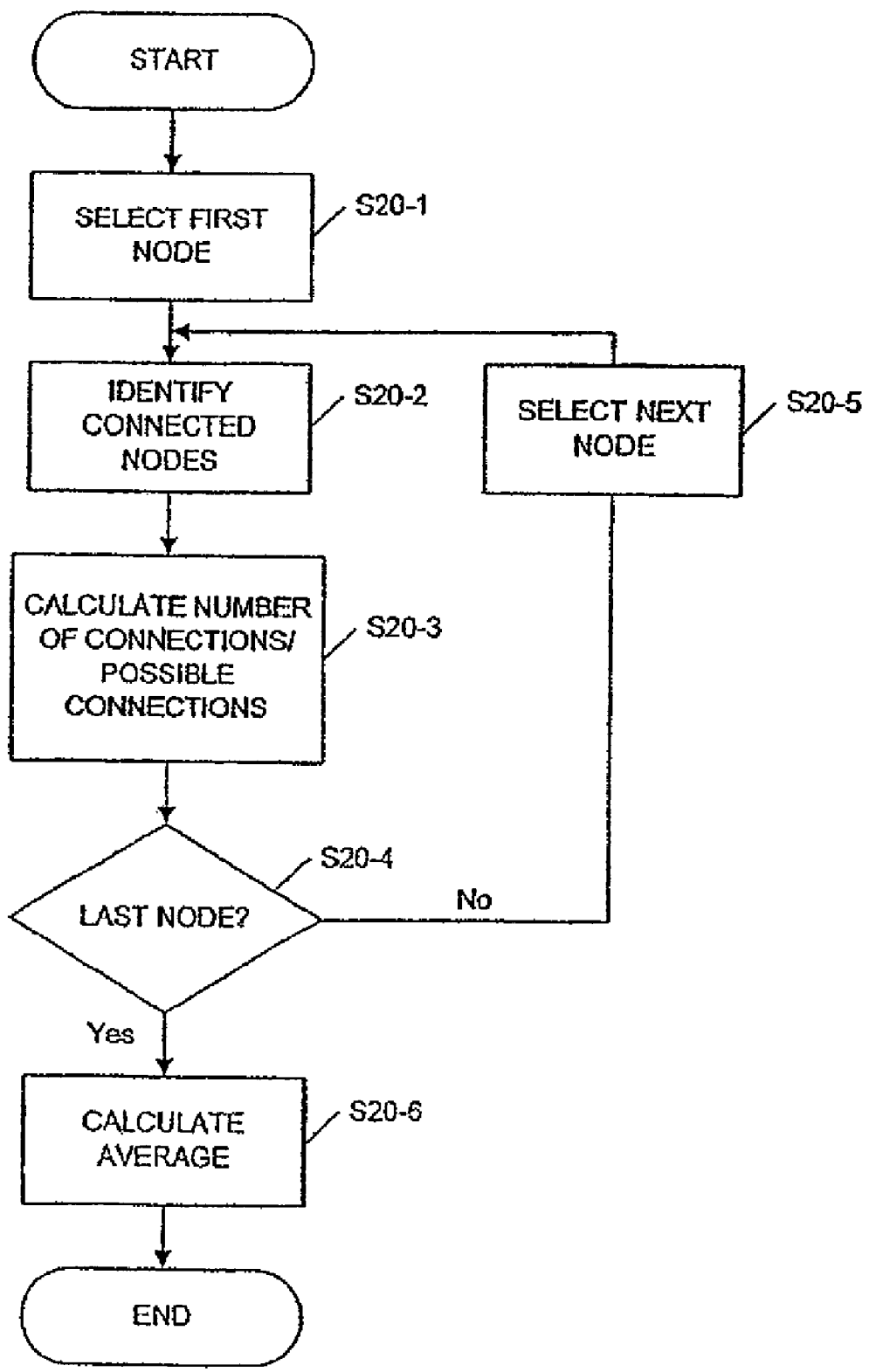
FIG. 20 is a flow diagram of the processing of the computer of FIG. 1 to calculate a connectivity coefficient for a network.

FIG. 19 is a flow diagram of the processing of the structural integrity analysis module 29 in order to determine average shortest path length measures.

Initially a first node record selected (S19-1). This will be the node record 40 associated with the lowest node number 41 which is not in the proposed set of deletions for which an average shortest path length is being determined Thus the first node record selected 40 will be 1 having a node number 41 equal to 1 unless the node number 1 is included in the proposed set of deletions for which the measure is being calculated.

The structural integrity analysis module 29 then (S19-2) identifies all the nodes to which the current node is connected. This is achieved by the structural integrity analysis module 29 utilising the list of connections 43 of the node record 40 for the currently selected node. Any of the nodes on the list of connections which do not correspond to nodes in the list of deletions for which a measure is being calculated and for which path length data has not yet been stored are then identified. A path length count is then incremented by one and path length data equal to the current path length count is stored for each of the newly identified nodes.

Thus for example if when processing node 1 it was determined that node 1 was connected to nodes 2, 3 and 4 and none of these nodes were in the set of proposed deletions, a value of 1 would be stored as a path length for nodes 2, 3 and 4 indicating that nodes 2, 3 and 4 could be reached in one link from node 1.

After path length data has been stored for all the newly identified nodes, the structural analysis integrity module 29 then (S19-3) determines whether path length data has been stored for all the nodes in the network with the exception of the node currently being processed and the node for the current proposed deletion for which the path length measure is being calculated.

If this is not the case the structural integrity analysis module 29 then (S19-4) determines whether processing the node records 40 currently selected for processing resulted in the identification of any new nodes for which path link data had not previously been stored. If this is not the case, this will mean that the structural integrity analysis module 29 will have established that the proposed set of deletions are such to divide the network into two or more separate networks. The structural integrity analysis module 29 then sets (S19-5) the average shortest path length for the network to a maximum value since there are some nodes for which node paths of any length exist which enables a pair of nodes to be connected.

If the structural integrity analysis nodule determines (S19-4) that at least some new nodes have been identified from processing the list of connected nodes 43 of the node records 40 for the currently selected nodes, the structural integrity analysis module 29 then (S19-6) selects all of the node records 40 having node numbers 41 for which path length data has just been stored and then (S19-2) utilises the list of connections 43 of all the newly selected nodes to determine and store path length data for any new nodes identified from these lists of connections 43.

Thus for example in the case of the network of FIG. 9, after storing path length data for nodes 2, 4 and 5, the lists of connected nodes 43 from the node records having node numbers 2, 4 and 5 would be selected. All the nodes identified by the lists of selected nodes 43 for the node records 40 having these node numbers 41 would then be identified. That is to say the following lists of connected nodes would be identified [1,3,7,8], [1,5,6], [1,4,8,9,10]. After merging the lists and deleting duplicates and nodes for which path length data had already been stored, the following nodes would be identified as new nodes [3,6,7,8,9,10]. Path length data of the value 2 would then be stored for these newly selected nodes. The structural integrity analysis module 29 then determines once again (S19-3) whether path length data has been stored for all the nodes and whether any path length data for new nodes has been stored (S19-4) before selecting further node records for generating shortest path length data.

Thus for example in the case of the exemplary network of FIG. 9 by virtue of the selection of nodes and storage of path length data, the following path length data would be stored for the nodes shown in FIG. 9 [–,1,2,1,1,2,2,2,2,2 etc] indicating that nodes 2, 4 and 5 are one link away from node 1, and nodes 3,6,7,8,9 and 10 are two links away from node 1.

When it is determined that path length data for the entire network identifying the shortest path length between the first node and all the other nodes has been stored, the structural integrity analysis module 29 then (S19-7) determines whether path length data for all nodes has been processed. If this is not the case, the structural integrity analysis module 29 then (S19-8) stores the calculated data for the node which has just been processed, resets the count value to zero and then proceeds to determine path length data utilising the next node number which is not a member of the set of deletions for which a value is currently being determined.

As a result of the processing by the structural integrity analysis module 29 eventually shortest path length data for all the nodes except those included in the current selection of deletions will be calculated and stored. The structural integrity analysis module 29 then (S19-9) proceeds to calculate the average value of all the path length data that has been stored. Thus in the case of the path length data for node 1 of FIG. 9 as set out above, an average path length of 1.3 would be calculated.

Returning to FIG. 18, after the average shortest path length for the network from which the proposed deletions have been removed have been calculated, the structural integrity analysis module 29 then (S18-2) calculates as a second measure of structural integrity, the number of disconnected nodes in the network. That is to say the structural integrity module 29 checks the list of connections 43 for each of the node records 40 and determines how many of those lists include no nodes or only nodes corresponding to the nodes of the proposed set of deletions. This number is then stored.

The structural integrity analysis module 29 then (S18-3) proceeds to calculate a connectivity coefficient for the network from which the proposed set of deletions have been removed as a third measure of the structural integrity of the network as will now be described in detail with reference to FIG. 20.

Initially the structural integrity analysis module 29 selects (S20-1) a first node for processing. This first node is the node for the lowest node number 41 which is not also in the set of proposed deletions.

When a node has been selected the structural integrity analysis module 29 then (S20-2) utilises the list of connected nodes 43 of the node record 40 having the selected node number 41 to identify the nodes that are connected to the selected node. The structural integrity analysis module 29 then removes from this list of identified nodes any nodes of the set of proposed deletions currently being processed.

The list of nodes from which any of the proposed deletions have been removed is then processed (S20-3) by the structural integrity analysis module 29 to determine the number of connections between the nodes in the list.

That is to say each of the nodes in the list is taken in turn and the structural integrity analysis module 29 checks the list of connections 43 for the node record 40 having a node number corresponding to the selected node number and identifies how many of the other nodes in the list appear in the list of connections 43 of the selected node record 40.

Thus for example if processing the node record associated with node 1 of the exemplary network of FIG. 9, utilising the list of connections 43 for node 1, nodes 2, 4 and 5 would be identified. Selecting and processing node 2 it would be determined that node 2 is not connected to either node 4 or node 5.

Conversely when processing node 4 it will be determined that node 4 is connected to node 5 and similarly node 5 is connected to node 4.

When the total number of connections between the nodes in the list of connections from which the proposed set of deletions have been removed has been calculated, a connectivity value is then determined by calculating the ratio of existing connections relative to the total number of possible connections between the nodes in the list.

Thus, for example, in the case of processing node 1 of FIG. 9 where node 1 is connected to three other nodes, two of which are connected to each other, a ratio of $$\frac{2}{3^2 - 3} = 0.33$$

More generally, when calculating a connectivity value for a node connected to n other nodes, the total number of connections between the nodes identified in the list of connections from which the proposed set of deletions is removed is calculated relative to the value (n2−n) being the total number of possible connections between n distinct nodes.

When a connectivity value for node has been calculated and stored, the structural integrity analysis module 29 then (S20-4) checks whether a connectivity value has been calculated for all of the nodes in the network except for those in the proposed set of deletions. If this is not the case the structural integrity analysis module 29 then (S20-5) selects the node record 40 having the next lowest node number 41 which is not in the proposed set of deletions and calculates and stores a connectivity value for that node.

When a connectivity value has been calculated for all of the nodes except for those in the proposed set of deletions, the structural integrity analysis module 29 then outputs (S20-6) as a measure of the structural integrity of the network a connectivity coefficient being equal to the average of all of the stored calculated connectivity values for the nodes in the network.

Returning to FIG. 17 at this stage the structural integrity analysis module 29 will have calculated three integrity measures for the network from which the proposed set of deletions has been removed. These three integrity measures being a measure of the average number of steps involved in the shortest paths between the nodes in the network, a measure of the number of disconnected nodes in the network and a connectivity coefficient indicative of the connectedness of the network.

When these measures have been calculated, the structural integrity analysis module 29 compares (S17-5) the integrity measures with the corresponding integrity measures for the unmodified set of deletions from which the modified set has been derived.

In this embodiment if the any of the integrity measures for the modified set of deletions is no worse than 10% worse than a corresponding measure for the unmodified data, which is to say the integrity measure is indicative of a network no more than 10% better connected than the network represented by an unmodified proposed set of deletions, the structural integrity analysis module 29 then (S17-6) proceeds to store the modified proposed set of deletions for further consideration, together with the values for the calculated integrity measures.

Either after storing data representing the modified proposed set of deletions (S17-6) or after determining (S17-5) that the modification of the proposed deletion data has resulted in integrity measures indicative of a network more than 10% better connected than the unmodified data, the structural integrity analysis module 29 checks (S17-7) whether all of the stored proposed sets of deletions have been processed and if this is not the case proceeds to select the next step of stored proposed deletions (S17-8) and randomly modifies that next set (S17-3). The structural integrity module 29 then determines whether to store the modified data (S17-4-S17-6) before checking once again whether the final set of proposed deletions has been reached (S17-7).

Eventually, when all of the stored sets of proposed deletions has been processed, the structural integrity analysis module 29 will have stored all of the proposed sets of deletions currently being considered and additionally modified sets of deletions where the modified deletions when the modified deletions are indicative of sets of deletions which are associated with integrity measures not more than 10% worse than those of the unmodified data.

At this stage, the structural integrity analysis module 29 proceeds to filter (S17-9) the stored data. In this embodiment this filtering is such to remove from storage any duplicate proposed sets of deletions and also either all proposed sets of deletions associated with integrity values any more than 35% worse than the integrity values associated with the sets of deletions resulting in the integrity values indicative of the most disconnected network, or alternatively is such to retain the proposed sets of deletions associated with the best fifty integrity values indicative of the greatest number of disconnected networks, whichever results in retaining the most proposed sets of deletions for further consideration.

After proposed sets of deletions associated with well connected networks have been removed, the structural integrity analysis module 29 then (S17-10) checks whether the number of iterations of processing of sets of proposed deletions has reached the final iteration. If this is not the case, the structural integrity analysis module 29 then once again selects the first stored set of proposed deletions and randomly modifies the selected set before determining whether or not to store the modified set of data (S17-1-S17-6) and then proceeds one after another to process each of the remaining stored sets of proposed deletions in the same way (S17-7-S17-6) before once again filtering the stored sets of data (S17-9) and determining whether the required number of iterations have now been completed (S17-10).

By generating a number of sets of proposed deletions in this way and processing sets of proposed deletions in accordance with the method illustrated in FIG. 17, the structural integrity analysis module 29 will cause to be stored data identifying those sets of deletions which most greatly effect the structural integrity of the network defined by data within the input store 10. Data identifying the best sets of deletions for affecting the structural integrity of the network is then stored in the target store. In this embodiment the top ten identified sets of proposed deletions for each number of deletions is stored within the target store 14.

Returning to FIG. 4 at this stage as a result of the processing of the target identifier 12, the target store 14 will have stored data identifying hub nodes, nodes involved in connections between sub networks, nodes which are difficult to route around, links that are difficult to route around or are involved in connections between sub networks and groups of nodes which together significantly effect the structural integrity of the network defined by the network data stored within the input store 10.

After the processing of the structural integrity analysis module 29 has been completed, the output module 18 is invoked (S4-8) which processes the data stored within the target store 14 utilising the filtration module 16 and the compound affinity database 20 to generate a report 4 as will now be described.

Specifically in this embodiment each of the nodes identified by data within the target store 14 is checked against the conservation database 30 and the critical protein store 32 to determine whether the node number identified by data stored within the target store corresponds to the node number 41 of a node record 40 identifying a protein 42 corresponding to a protein stored within the conservation database 30 or the critical protein store 32.

In this way the output module 28 is able to classify each of the items of data stored within the target store 14 as either relating to critical proteins identified by data within the critical protein store 32, proteins corresponding to proteins identified by the conservation database 30 or neither of these.

The output module 18 then generates and outputs a report 4 which identifies the proteins corresponding to the node numbers stored within the target store 14 where the proteins which are determined not to appear in either of the conservation database 30 or the critical protein store 32 are listed separately from those which are determined to appear in the conservation database 30 or the critical protein store 32.

Figure 21:
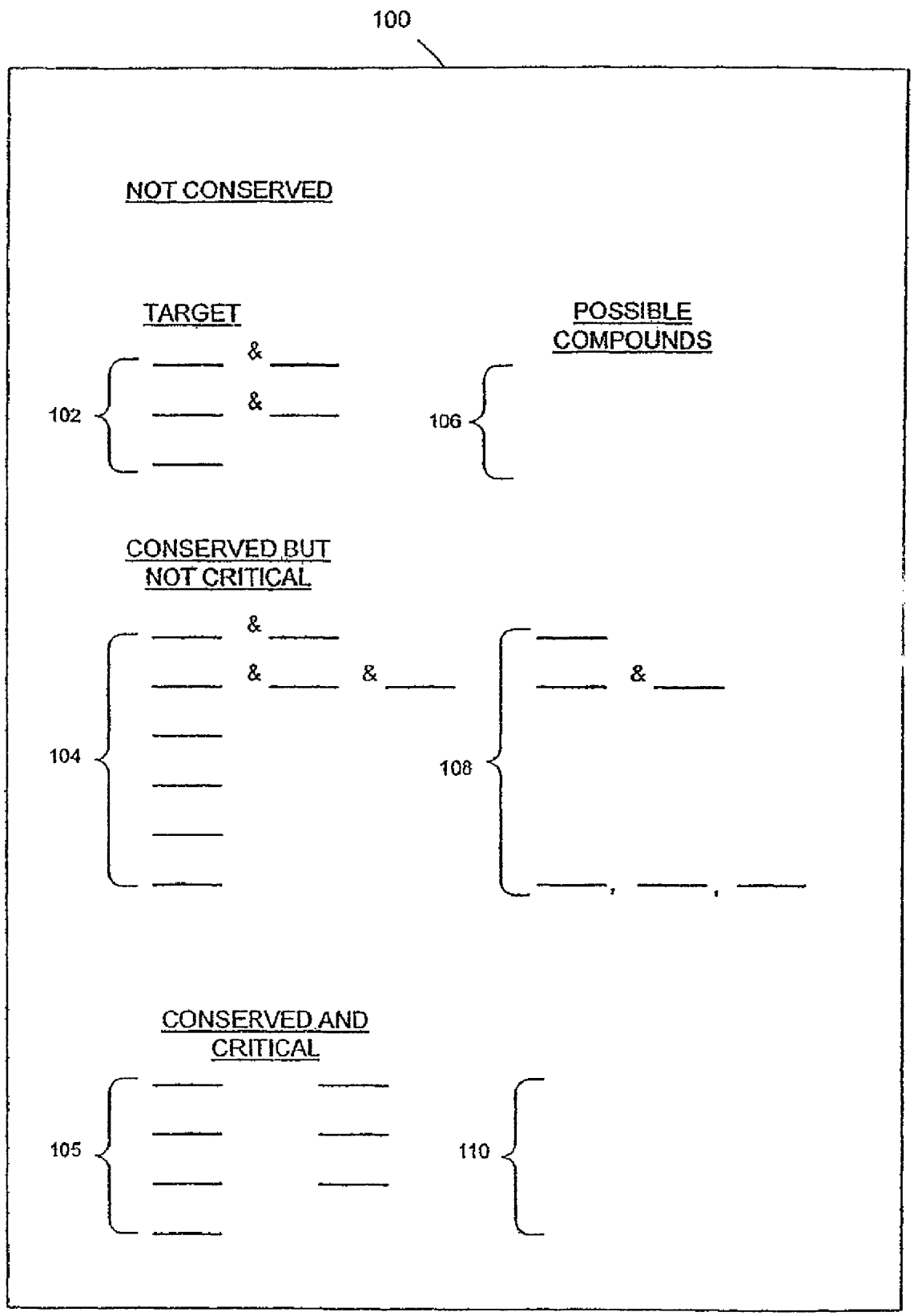
FIG. 21 is a schematic illustration of a report identifying possible cellular targets for pharmaceutical compounds.

FIG. 21 is a schematic illustration of a report 100 generated by the output module 18.

In this embodiment the report 100 comprises three lists 102, 104, 105 where the first list 102 identifies proteins identified by data stored in the target store 14 for which no corresponding entries are stored within the conservation database 30 or critical protein store 32; a second list 104 which identifies proteins identified by data stored within the target store 14 where any of the nodes or nodes within the groups of nodes are identified by data within the conservation database 30 but not the critical protein store 32; and a third list 105 which identifies the remaining proteins identified by data in the target store 14.

In this embodiment adjacent to each of these lists is a further list 106, 108, 110. Each of these lists identify for the corresponding list within the report 100 any compounds known to react with proteins identified in the list as identified by data within the compound affinity database 20. Thus in this way the output module 18 is able to generate a report where possible target proteins are identified based on an analysis of the topology of network data input into the input store 10.

Modifications and Amendments

In the above described embodiment, a filtration module 16 is described as including a critical protein store 32 identifying critical proteins for the functioning of a host organism. The data entered into the critical protein store could be obtained through conventional sources. Alternatively the system described in the first embodiment could be utilised to identify critical proteins.

Specifically instead of entering proteome data into the input store 10 representative of the proteome of an organism to be attacked, proteome data for the host organism could be entered into the input store. When this host organism proteome data was processed, the target identifier 12 would then proceed to identify hubs, nodes and links involved in connection between sub networks, nodes and links that are difficult to route around and second order nodes and groups of nodes which affect the structure integrity of the network represented in the host organism proteome.

Just as in the case of processing proteome data representative of an organism to be attacked, this processing will identify nodes, links and groups of nodes which are important for the structural integrity of the host organism proteome. By generating data in this way identification of critical proteins, links and groups of protein for a hosting organism could then be achieved.

More generally whenever two networks interact with one another by processing data representative of a first network and storing data identifying critical elements in that first network and then processing data for the second network, it is possible to identify critical elements in the second network, interference with which is less likely to effect the functioning of the first network.

Although in the above embodiment the functioning of the structural integrity analysis module 29 is described as making random selection for nodes for inclusion in sets of proposed deletion where the selection of nodes is made from any of the nodes identified by data within the input store 10, the selection of nodes could be more restricted. One way in which the selection of nodes for proposed sets of deletion could be restricted is by having the structural integrity analysis module 29 select sets of proposed deletions from the nodes stored within the target store 14 as being potentially critical nodes identified by the hub identification module 22, sub identification network module 24, bottleneck identification module 26, critical path identification module 27 and second order node identification module 28. An advantage of such a system is that since only a subset of the total number of nodes representing a network can be selected from, the speed of processing of the structure integrity analysis module 29 would be greatly increased.

The restriction of the selection of nodes by the structural integrity analysis module 29 to nodes identified by the other module of the target identifier 12 could either be made so as to restrict the generation of initial sets of proposed deletions, or alternatively to restrict both the generation of initial sets of proposed deletion and subsequent proposed modifications of the sets made by the structural integrity analysis module 29.

A further way in which the processing of the structural integrity analysis module 29 could be restricted would be to prevent the structural integrity analysis module 29 from including within proposed sets of deletions any protein identified by the critical protein store 32. Where the critical protein store 32 stores data identifying critical proteins for a host organism by preventing the structural integrity analysis module 29 included within groups of proposed deletion proteins corresponding to critical proteins, the structural integrity analysis module 29 would then generate groups of proposed deletion which effect the structural integrity of the proteome defined by the data stored within the input store 10 but which do not include deletions which are likely to effect the structural integrity of a host.

A further alternative would be to cause the structural integrity analysis module 29 to select proteins for inclusion within the groups of proposed deletion for which compounds known to react with those proteins are identified by data within the compound affinity database 20. In this way together the structural integrity analysis module 29 and the output module 18 would generate groups of proposed compounds known to interact with proteins in the proteome and the target organism which affect the structural integrity of the proteome and hence will propose groups of compounds which are likely to be suitable for therapies.

Although in the above described embodiment, the input of data corresponding to a proteome has been described, it will be appreciated that where compounds affecting the interactions of specific proteins have already been identified, proteome data excluding the interactions of a specific protein or group of proteins could be input into the input store 10. The computer 2 would then be able to identify additional targets to complement the activity of the known compound or compounds. Thus in this way when a potential compound has been found to have some activity, complementary targets for therapy could then be identified.

In the above described embodiment, a value is calculated for each node in a network identifying the number of connections a node has, the extent to which a node can be easily bypassed, the extent to which a node forms part of a link between sub networks and the extent to which a node is connected to other nodes of importance. In the embodiment these values are described as being utilised to select nodes as being of importance for the structural integrity of a network. It will appreciated that instead of selecting a number of nodes associated with the best scores as is described in the embodiment, these values could instead be utilised to rank the nodes in an order. Alternatively a weighting value ranking the node based on more than one measure of the Importance of the node for a network's structural integrity could be utilised to enable nodes to be selected for further analysis.

In the above described embodiment, in determining whether a node can be bypassed, determination of a number of paths between connected nodes having five elements is described. It will be appreciated that paths of up to any suitable threshold could be identified and a redundancy ratio calculated on the basis of paths of that length.

In the above described embodiment, two methods are described for dividing a network into a number of sub networks. It will be appreciated that a number of alternative techniques could be used to assign individual nodes to different sub networks so that connections between sub networks could be identified. Suitable methods will include statistical methods such as non metric multi dimensional scaling, correspondence analysis, chi squared analysis and varieties of factor analysis such as principal components and independent components analysis. In addition optimal set analysis could be used as well as a variety of optimization based methods for determining the organisation of a complex system into sub networks.

More generally it will be appreciated that any suitable method based on the principle that nodes should be assigned the same sub network as other nodes having similar patterns of connections could be utilised.

In the described embodiment, the selection of groups of proposed deletions is made on the basis of determining three measurements of network integrity. It will be appreciated that selections of proposed deletions could of course be made solely on the basis of a single measure of network integrity. It is preferred that more than one measure is utilised since the different measures measure different aspects of the connectivity of a network.

In other embodiments, other values indicative of network integrity could be calculated for networks and used to identify sets of proposed deletions that have a significance effect on the overall integrity of a network.

Although in the above described embodiment reference has been made to identifying nodes directly connected to nodes in different sub networks or directly connected to other nodes of importance, it will be appreciated that nodes connected via short paths to such nodes could be identified.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means.

When a program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

The invention claimed is:

1. A method of network analysis comprising:
   obtaining data defining interactions between a set of elements;
   storing the data as network data wherein the network data defines a network comprising a plurality of nodes and a plurality of links between the nodes;
   generating data defining a plurality of groups of nodes of the stored network data;
   determining for each of the plurality of groups of nodes one or more values indicative of the extent to which removal of the group of nodes from the network affects the structural integrity of the network;
   generating further data identifying further groups of nodes;
   processing the network data to determine for each of the further groups of nodes one or more values indicative of the extent to which removal of the further groups from the network affects the structural integrity of the network;
   identifying the groups of nodes from the plurality of groups of nodes and the further groups of nodes associated with values above a threshold value; and
   outputting data identifying groups of target elements identifying groups of elements corresponding to the identified groups of nodes associated with values above said threshold value.

2. The method of claim 1, wherein the method includes calculating for each of the groups of nodes the average shortest path length between nodes in the network not in the groups via links not connected to the nodes in the groups.

3. The method of claim 1, wherein the method includes calculating for each of the groups of nodes a connectivity coefficient for the network defined by stored data in the absence of the nodes in the groups and links to nodes in the groups.

4. The method of claim 1, wherein the determining one or more values comprises calculating for each of the groups of nodes the number of the nodes connected only to nodes in the groups.

5. The method of claim 1, wherein the generation of further groups comprises:
    storing data defining a set of nodes and generating the further groups of nodes by randomly modifying the groups of nodes by swapping one or more nodes of the defined groups of nodes with one or more nodes selected from the nodes in the set of nodes defined by stored data.

6. The method of claim 5, wherein the set comprises nodes selected from a group comprising:
    nodes of the network associated with a greater than average number of links for the network;
    nodes of the network associated with links between sub networks of nodes wherein the sub networks of nodes are more connected with other members of the same sub network than with nodes in different sub networks;
    nodes of the network for which the number of paths between other nodes which pass through the nodes relative to the number of paths between other nodes which do not pass through the nodes is greater than another threshold value; and
    nodes of the network, connected to any of the above the nodes.

7. The method of claim 1, wherein the generation of further groups comprises:
    storing data defining a set of excluded nodes; and
    generating the further groups of nodes by modifying groups of nodes by swapping one or more nodes of the defined group of nodes with one or more nodes which are not identified by the stored data defining the set of excluded nodes.

8. The method of claim 7, further comprising:
    storing network data defining a plurality of nodes and a plurality of links for a second network;
    identifying for the stored network data for the second network, a set of nodes selected from a group comprising:
    nodes associated with a greater than average numbers of links for the second network;
    nodes associated with links between sub networks of nodes of the second network wherein the sub networks of nodes are more connected with other members of the same sub network than with nodes in different sub networks;
    nodes for which the number of paths between other nodes which pass through the nodes relative to the number of paths between other nodes which do not pass through the nodes is greater than a further threshold value; and
    nodes in the second network, connected to any of the above nodes; and
    storing as data defining the set of excluded nodes data identifying nodes in the network corresponding to the identified set of nodes of the second network.

9. A method of manufacturing a drug therapy comprising:
    identifying groups of target proteins for drug therapies by:
        obtaining proteome data defining a set of protein interactions for an organism to be targeted;
        storing the proteome data as network data wherein the network data defines a network comprising a plurality of nodes and a plurality of links between the nodes;
        generating data defining a plurality of groups of nodes of the stored network data;
        determining for each of the plurality of groups of nodes one or more values indicative of the extent to which removal of the group of nodes from the network effects the structural integrity of the network;
        generating further data identifying further groups of nodes;
        processing the network data to determine for each of the further groups of nodes one or more values indicative of the extent to which removal of the further groups from the network affects the structural integrity of the network;
        identifying the groups of nodes from the plurality of groups of nodes and the further groups of nodes associated with values above a threshold value;
        outputting data identifying groups of target elements identifying groups of elements corresponding to the identified groups of nodes associated with values above said threshold value;
        identifying compounds which react with proteins associated with the nodes of an identified group; and
        manufacturing a drug therapy containing compounds identified as reacting with the identified group of proteins.

10. The method of claim 9, further comprising:
    obtaining proteome data defining a set of protein interactions for a host organism;
    storing the proteome data as network data for a second network wherein the network data defines a network comprising a plurality of nodes and a plurality of links between the nodes;
    identifying for the stored network data for the second network, a set of nodes selected from a group comprising:
    nodes associated with a greater than average numbers of links for the second network;
    nodes associated with links between sub networks of nodes of the second network wherein the sub networks of nodes are more connected with other members of the same sub network than with nodes in different sub networks;
    nodes for which the number of paths between other nodes which pass through the nodes relative to the number of paths between other nodes which do not pass through the nodes is greater than another threshold value; and
    nodes in the second network, connected to any of the above nodes; and
    storing as data defining the set of excluded nodes data identifying nodes in the network corresponding to the identified set of nodes of the second network;
    wherein generating the further groups of nodes comprises modifying groups of nodes by swapping one or more nodes of the defined group of nodes with one or more nodes which are not identified by the stored data defining the set of excluded nodes.

11. An information processing apparatus for processing data defining interactions between a set of elements, the apparatus comprising:
    a data store operable to store data defining interactions between a set of elements in the form of network data defining a network comprising a plurality of nodes and a plurality of links between the nodes;
    a generator operable to generate data defining a plurality of groups of nodes defined by data stored in the data store;
    an assessment module operable to associate each group of nodes defined by data generated by the generator with one or more values indicative of the extent to which removal of the groups of nodes identified by data generated by the generator affects the structural integrity of the network defined by the data stored in the data store;
    a selection module operable to identify groups of nodes associated with values by the assessment module above a threshold value; and an output module operable to output data identifying groups of elements corresponding to groups of nodes identified by the selection module.

12. The apparatus of claim 11, wherein the assessment module is operable to determine as a value indicative of the extent removal of nodes affects network integrity the average shortest path length between nodes in the network not in the group via links not connected to the nodes in the group.

13. The apparatus of claim 11, wherein the assessment module is operable to determine as a value indicative of the extent removal of nodes affects network integrity, a connectivity coefficient for the network defined by stored data in the absence of the nodes in the group and links to nodes in the group.

14. The apparatus of claim 11, wherein the assessment module is operable to determine as a value indicative of the extent removal of nodes affects network integrity the number of the nodes connected only to nodes in the group.

15. The apparatus of claim 11, wherein the generator comprises:
a node store operable to store data defining a set of nodes, the generator being arranged to generate groups of nodes by randomly modifying previously generated groups of nodes by swapping one or more nodes of the defined groups of nodes with one or more nodes selected from the nodes in the set of nodes defined by data stored in the node store.

16. The apparatus of claim 15, wherein the node store is arranged to store data defining a set of nodes selected from a group comprising:
nodes of the network associated with a greater than average number of links for the network;
nodes of the network associated with links between sub networks of nodes wherein the sub networks of nodes are more connected with other members of the same sub network than with nodes in different sub networks;
nodes of the network for which the number of paths between other nodes which pass through the nodes relative to the number of paths between other nodes which do not pass through the nodes is greater than another threshold value; and
nodes of the network, connected to any of the above the nodes.

17. The apparatus of claim 11, wherein the generator comprises:
an excluded nodes store operable to storing data defining a set of excluded nodes, the generator being arranged to generate groups of nodes by modifying previously generated groups of nodes by swapping one or more nodes of the defined group of nodes with one or more nodes which are not identified by the stored data stored in the excluded nodes store.

18. A non-transitory storage medium having computer executable instructions to direct a programmable computer to:
obtain data defining interactions between a set of elements;
store the data as network data wherein the network data defines a network comprising a plurality of nodes and a plurality of links between the nodes;
generate data defining a plurality of groups of nodes of the stored network data;
determine for each of the plurality of groups of nodes one or more values indicative of the extent to which removal of the group of nodes from the network effects the structural integrity of the network;
generate further data identifying further groups of nodes;
process the network data to determine for each of the further groups of nodes one or more values indicative of the extent to which removal of the further groups from the network affects the structural integrity of the network;
identify the groups of nodes from the plurality of groups of nodes and the further groups of nodes associated with values above a threshold value; and
output data identifying groups of target elements identifying groups of elements corresponding to the identified groups of nodes associated with values above said threshold value.

\* \* \* \* \*